US008470325B2

(12) United States Patent
Ando et al.

(10) Patent No.: US 8,470,325 B2
(45) Date of Patent: Jun. 25, 2013

(54) METHOD OF TREATING AMYKLOIDOSIS COMPRISING ADMINISTERING AN ANTI-HMGB-1 ANTIBODY

(75) Inventors: Yukio Ando, Kumamoto (JP); Ikuro Maruyama, Kagoshima (JP); Shingo Yamada, Tokyo (JP)

(73) Assignees: Kagoshima University, Kagoshima (JP); Kumamoto University, Kumamoto (JP); Shino-Test Corporation, Tokyo (JP)

( * ) Notice: Subject to any disclaimer, the term of this patent is extended or adjusted under 35 U.S.C. 154(b) by 54 days.

(21) Appl. No.: 12/449,543

(22) PCT Filed: Feb. 15, 2008

(86) PCT No.: PCT/JP2008/052500
§ 371 (c)(1),
(2), (4) Date: Jul. 1, 2010

(87) PCT Pub. No.: WO2008/099913
PCT Pub. Date: Aug. 21, 2008

(65) Prior Publication Data
US 2011/0229487 A1  Sep. 22, 2011

(30) Foreign Application Priority Data
Feb. 15, 2007 (JP) ................ 2007-034325

(51) Int. Cl.
*A61K 39/395* (2006.01)
*A61K 39/00* (2006.01)
*C07K 16/24* (2006.01)
*C07K 16/18* (2006.01)

(52) U.S. Cl.
USPC .......... 424/145.1; 424/130.1; 424/139.1; 530/388.23; 530/387.1; 530/387.9

(58) Field of Classification Search
None
See application file for complete search history.

(56) References Cited

U.S. PATENT DOCUMENTS

| 6,303,321 | B1 | 10/2001 | Tracey et al. |
| 6,448,223 | B1 | 9/2002 | Tracey et al. |
| 6,468,533 | B1 | 10/2002 | Tracey et al. |
| 6,713,450 | B2 | 3/2004 | Frangione et al. |
| 6,822,078 | B2 | 11/2004 | Ozaki et al. |
| 7,220,723 | B2 | 5/2007 | Tracey et al. |
| 7,304,034 | B2 | 12/2007 | Tracey et al. |
| 2003/0060410 | A1 | 3/2003 | Tracey et al. |
| 2003/0091995 | A1 | 5/2003 | Buechler et al. |
| 2004/0005316 | A1 | 1/2004 | Tracey et al. |
| 2004/0141948 | A1 | 7/2004 | O'Keefe |
| 2004/0229279 | A1 | 11/2004 | Ozaki et al. |
| 2004/0242481 | A1 | 12/2004 | Bianchi et al. |
| 2006/0099207 | A1 | 5/2006 | Wu et al. |
| 2007/0238640 | A1 | 10/2007 | Tracey et al. |
| 2008/0045455 | A1 | 2/2008 | Mjalli et al. |
| 2008/0167234 | A1 | 7/2008 | Tracey et al. |
| 2008/0214454 | A1 | 9/2008 | Tracey et al. |
| 2010/0173277 | A1 | 7/2010 | Yasunami et al. |
| 2010/0216977 | A1 | 8/2010 | Kuwano et al. |

FOREIGN PATENT DOCUMENTS

| CA | 2470640 A1 | 6/2003 |
| JP | 62-166897 A | 7/1987 |
| JP | 10-319019 | 12/1998 |
| JP | 2003-096099 A | 4/2003 |
| JP | 2003-534351 A | 11/2003 |
| JP | 2004-107260 A | 4/2004 |
| JP | 2005/508913 A | 4/2005 |
| JP | 2008-520552 A | 6/2008 |
| WO | WO 96/25493 A1 | 8/1996 |
| WO | WO 98/02744 A1 | 1/1998 |
| WO | WO 00/47104 A2 | 8/2000 |
| WO | WO 02/074337 A1 | 9/2002 |
| WO | WO 02/092004 A2 | 11/2002 |
| WO | WO 03/026691 A2 | 4/2003 |
| WO | WO 03/051383 A2 | 6/2003 |
| WO | WO 2004/004763 A2 | 1/2004 |
| WO | WO 2004/044001 A2 | 5/2004 |
| WO | WO 2004/046338 A2 | 6/2004 |
| WO | WO 2004/046345 A2 | 6/2004 |
| WO | WO 2005/026209 A2 | 3/2005 |
| WO | WO 2005/074984 A1 | 8/2005 |
| WO | WO 2006/124477 A2 | 11/2006 |
| WO | WO 2006/138429 A2 | 12/2006 |
| WO | WO 2007/001422 A2 | 1/2007 |
| WO | WO 2007/130302 A2 | 11/2007 |

OTHER PUBLICATIONS

Merlini et al. (2011). Amyloidosis: pathogenesis and new therapeutic options. Journal of Clinical Oncology. 29(14):1924-1933.*
Mihara et al. (2004). Anti-Interleukin 6 receptor antibody inhibits murine AA-amyloidosis. The Journal of Rheumatology. 31(6):1132-1138.*
Andersson, U., et al., "High Mobility Group 1 Protein (HMG-1) Stimulates Proinflammatroy Cytokine Synthesis in Human Monocytes," *J. Exp. Med.* 4:565-570, The Rockeffer University Press (2000).
Lachmann, H.J. and Hawkins, P.N., "Systemic amyloidosis," *Current Opinion in Pharmacology* 6:214-220, Elsevier Ltd. (2006).

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

Previously, it was difficult to obtain high-affinity antibodies that specifically bind to HMGB-1 but not to HMGB-2. Under this circumstance, the present inventors successfully obtained antibodies that are more reactive to HMGB-1 than to HMGB-2 by using specific peptides as an antigen. The present inventors also demonstrated that the antibodies had a HMGB-1-neutralizing activity. The present inventors administered the antibodies to amyloidosis model animals, and as a result, successfully demonstrated that the antibodies produced a significant therapeutic effect.

4 Claims, 7 Drawing Sheets
(2 of 7 Drawing Sheet(s) Filed in Color)

OTHER PUBLICATIONS

Park, J.S., et al., "Involvement of Toll-like Receptors 2 and 4 in Cellular Activation in High Mobility Group Box 1 Protein," *J. Biological Chemistry* 279:7370-7377, The American Society for Biochemistry and Molecular Biology, Inc. (2004).

Scaffidi, P., et al., "Release of chromatin protein HMGB1 by necrotic cells triggers inflammation," *Nature* 418:191-195, Nature Publishing Group (2002).

Ueno, H., et al., "Contributions of High Mobility Group Box Protein in Experimental and Clinical Acute Lung Injury," *Am. J. Respir. Crit. Care Med.* 170:1310-1316, American Thoracic Society (2004).

Wang, H., et al., "HMG-1 as a Late Mediator of Endotoxin Lethality in Mice," *Science* 285:248-251, National Academy of Sciences (1999).

Wen, L., et al., "A human placental cDNA clone that encodes nonhistone chromosomal protein HMG-1," *Nucleic Acids Research* 17:1197-1214, Oxford Journals (1989).

Yamada, S., et al., "High Mobility Group Protein 1 (HMGB1) Quantified by ELISA with a Monoclonal Antibody That Does Not Cross-React with HMGB2," *Clinical Chemistry* 49:1535-1537, American Association of Clinical Chemists (2003).

International Search Report for International Appl. No. PCT/JP2008/052500, Japanese Patent Office, Tokyo, mailed on May 1, 2008.

Esp@cenet English language abstract for Japanese Patent Publication No. JP 62-166897 A (listed as document FP1 on PTO/SB/08A), 1987.

Esp@cenet English language abstract for Japanese Patent Publication No. JP 10-319019 A (listed as document FP4 on PTO/SB/08A), 1998.

Esp@cenet English language abstract for Japanese Patent Publication No. JP 2003-096099 A (listed as document FP8 on PTO/SB/08A), 2003.

Co-pending U.S. Appl. No. 12/449,562, filed Feb. 15, 2008, inventors Kuwano, K., et al. (Not Yet Published).

Co-pending U.S. Appl. No. 12/527,159, filed Feb. 15, 2008, inventors Yasunami, Y., et al. (Not Yet Published).

Concise Explanation of Japanese Reference JP 62-166897 A, published Jul. 23, 1987.

Concise Explanation of Japanese Reference JP 10-319019, published Dec. 4, 1998.

Concise Explanation of Japanese Reference JP 2003-096099 A, published Apr. 3, 2003.

Fossati, S. and Chiarugi, A., "Relevance of High-Mobility Group Protein Box 1 to Neurodegeneration," *Int. Rev. Neurobiol.* 82:137-148, Elsevier Inc., United States (2007).

Kallijärvi, J., et al., "Amphoterin Includes a Sequence Motif Which is Homologous to the Alzheimer's β-Amyloid Peptide (Aβ), Forms Amyloid Fibrils in Vitro, and Binds Avidly to Aβ," *Biochem.* 40:10032-10037, American Chemical Society, United States (2001).

Lotze, M.T. and Tracey, K.J., "High-Mobility Group Box 1 Protein (HMGB1): Nuclear Weapon in the Immune Arsenal," *Nat. Rev. Immunol.* 5:331-342, Nature Publishing Group, England (2005).

Takata, K., et al., "High Mobility Group Box Protein-1 Inhibits Microglial Aβ Clearance and Enhances Aβ Neurotoxicity," *J. Neurosci. Res.* 78:880-891, Wiley-Liss, Inc., United States (2004).

Supplementary European Search Report for European Application No. EP 08 71 1330, Munich, Germany, completed on Sep. 1, 2011.

Kim, J.Y., et al., "HMGB1 contributes to the development of acute lung injury after hemorrhage," *Am. J. Physiol. Lung Cell Mol. Physiol.* 288:L958-L965, The American Physiological Society, United States (2005).

Unoshima, M., "Therapeutic effect of anti—HMGB1 antibody and anti—RAGE antibody on SIRS/sepsis," *Nihon Rinsho* 62(12):2323-2329, Nihon Rinsho Co., Japan (2004).

Unverified English Language Translation of: Unoshima, M., "Therapeutic effect of anti—HMGB1 antibody and anti—Rage antibody on SIRS/sepsis," *Nihon Rinsho* 62(12):2323-2329, Nihon Rinsho Co., Japan (2004), 9 pages.

Wang, H., et al., "Extracellular role of HMGB1 in inflammation and sepsis," *J. Intern. Med.* 255:320-331, Blackwell Publishing Ltd., England (2004).

Wang, H., et al., "HMGB1 as a late Mediator of Lethal Systemic Inflammation," *Am. J Respir. Crit. Care Med.* 164:1758-1773, American Lung Association, United States (2001).

Cohen, A.S., "Endocrine and Metabolic Disorders," in Amyloidosis: Merck Manual Professional, 4 pages, Merck Sharp & Dohme Corp., USA, www.merckmanuals.com/professional/print/endocrine_and_metabolic_disorders/amyloidosis/amyloidosis.html (Apr. 2008).

Ueda, M., et al., "FK506 Inhibits Murine AA Amyloidosis: Possible Involvement of T Cells in Amyloidogenesis," *J. Rheumatol.* 33:2260-2270, The Journal of Rheumatology Publishing Co., Ltd., Toronto, Canada (2006).

Corry, R.J. et al., "Primarily Vascularized Allografts of Hearts in Mice. The Role of H-2D, H-2K, and Non-H-2 Antigens in Rejection," *Transplantation* 16:343-350, The Williams & Wilkins Co. (1973).

Cortez-Retamozo, V. et al., "Efficient Tumor Targeting by Single-Domain Antibody Fragments of Camels," *Int. J. Cancer* 98:456-462, Wiley-Liss, Inc. (2002).

Dumitriu, I.E. et al., "Release of High Mobility Group Box 1 by Dendritic Cells Controls T Cell Activation via the Receptor for Advanced Glycation End Products," *J. Immunol.* 174:7506-7515, The American Association of Immunologists, Inc. (2005).

*GEN News Highlights*, "Nautilus Biotech and Creabilis Therapeutics Partnership Achieve Technical Milestone," Nov. 14, 2006; available at http://www.genengnews.com/gen-news-highlights/nautilus-biotech-and-creabilis-therapeutics-partnership-achieve-technical-milestone/8849754.

Hsu, L.-W. et al., "The effects of anti-histone H1 antibody on immune cells responsible for rejection reaction," *Mol. Immunol.* 42:1155-1164, Elsevier Ltd. (2004).

Itoh, T. et al., "A Novel Mechanism Involved in Early Loss of Transplanted Islets in the Liver Mediated by HMGB1," *Diabetes* 58:A18-A19, No. 67-OR, American Diabetes Association (2009).

Kaczorowski, D.J. et al., "Mechanisms of Toll-Like Receptor 4 (TLR4)-Mediated Inflammation After Cold Ischemia/Reperfusion in the Heart," *Transplantation* 87:14551463, Lippincott Williams & Wilkins (2009).

Kawahara, K-i et al., "HMGB1 release in co-cultures of porcine endothelial and human T cells," *Xenotransplantation* 14:636-641, Blackwell Munksgaard (2007).

Matsuoka, N. et al., "High-mobility group box 1 is involved in the initial events of early loss of transplanted islets in mice," *J. Clin. Invest.* 120:735-743, American Society for Clinical Investigation (2010).

Nakano, T. et al., "Experimental and Clinical Significance of Antinuclear Antibodies in Transplantation," *Transplantation* 83:1122-1125, Lippincott Williams & Wilkins (2007).

"Cell Motility in Cancer Invasion and Metastasis" in *Cancer Metastasis—Biology and Treatment*, vol. 8, Wells, A., ed., pp. 286-287, Springer (2006).

Yamazaki, C. et al., "Effect of Lecithinized-Superoxide Dismutase on the Interstitial Pneumonia Model Induced by Bleomycin in Mice," *Jpn. J. Pharmacol.* 75:97-100, Japanese Pharmacological Society (1997).

Abdelaziz, M.M., et al., "Treatment of idiopathic pulmonary fibrosis: Is there anything new?," *Respirology* 10:284-289, Blackwell Science (2005).

Abraham, E., et al., "Cutting Edge: HMG-1 as a Mediator of Acute Lung Inflammation," *J. Immunol.* 165:2950-2954, The American Association of Immunologists (2000).

Banerjee, S., and Kundu, T.K., "The acidic C-terminal domain and A-box of HMGB-1 regulates p53-mediated transcription," *Nucleic Acid Res.* 31:3236-3247, Oxford University Press (2003).

Goldstein, D.R., "The Identity of Innate Immune Activators in Organ Transplantation: Origins from Within or Exterior to the Host?," *Am. J. Transplant.* 7:1692-1694, The American Society of Transplantation and the American Society of Transplant Surgeons (2007).

Huang, Y., et al., "Extracellular Hmgb1 Functions as an Innate Immune-Mediator Implicated in Murine Cardiac Allograft Acute Rejection," *Am. J. Transplant.* 7:799-808, The American Society of Transplantation and the American Society of Transplant Surgeons (2007).

International Consensus Statement "Idiopathic Pulmonary Fibrosis: Diagnosis and Treatment,", *Am. J Respir. Crit. Care Med.* 161:646-664, American Thoraic Society and European Respiratory Society (2000).

Moser, B., et al., "Blockade of RAGE Suppresses Alloimmune Reactions in Vitro and Delays Allograft Rejection in Murine Heart Transplantation," *Am. J. Transplant.* 7:293-302, The American Society of Transplantation and the American Society of Transplant Surgeons (2007).

Nakano, T., et al., "Experimental and Clinical Significance of Antinuclear Antibodies in Liver Transplantation," *Transplantation* 83:1122-1125, Lippincott Williams & Wilkins (2007).

Rovere-Querini, P., et al., "HMGB1 is an endogenous immune adjuvant released by necrotic cells," *EMBO reports* 5:825-830, European Molecular Biology Organization (2004).

Shapiro, A.M.J., et al., "Clinical islet transplant: current and future directions towards tolerance," *Immunol. Reviews* 196:219-236, Blackwell Munksgaard (2003).

Yamahara, K., et al., "High-Mobility Group Box 1 Protein (HMGB1) Released by Cell Transplantation Plays an Important Role in the Therapeutic Effects for Treating Chronic Ischemic Heart Failure," *Circulation* 114 (*Supp. II*):566-567, Abstract 2716, Abstracts from Scientific Sessions (2006).

Office Action mailed Jan. 24, 2012, in U.S. Appl. No. 12/527,159, inventors Yasunami, Y., et al., Int'l Filing Date of Feb. 15, 2008, U.S. Patent and Trademark Office, Alexandria, VA.

Amendment and Reply submitted Mar. 22, 2012, in U.S. Appl. No. 12/527,159, inventors Yasunami, Y., et al., Int'l Filing Date of Feb. 15, 2008, U.S. Patent and Trademark Office, Alexandria, VA.

Office Action mailed Apr. 20, 2012, in U.S. Appl. No. 12/527,159, inventors Yasunami, Y., et al., Int'l Filing Date of Feb. 15, 2008, U.S. Patent and Trademark Office, Alexandria, VA.

Amendment and Reply submitted Jun. 18, 2012, in U.S. Appl. No. 12/527,159, inventors Yasunami, Y., et al., Int'l Filing Date of Feb. 15, 2008, U.S. Patent and Trademark Office, Alexandria, VA.

Office Action mailed Jul. 26, 2012, in U.S. Appl. No. 12/527,159, inventors Yasunami, Y., et al., Int'l Filing Date of Feb. 15, 2008, U.S. Patent and Trademark Office, Alexandria, VA.

Amendment and Reply submitted Nov. 2, 2012, in U.S. Appl. No. 12/527,159, inventors Yasunami, Y., et al., Int'l Filing Date of Feb. 15, 2008, U.S. Patent and Trademark Office, Alexandra, VA.

Office Action mailed Jan. 24, 2012, in U.S. Appl. No. 12/449,562, inventors Kuwano, K., et al., Int'l Filing Date of Feb. 15, 2008, U.S. Patent and Trademark Office, Alexandria, VA.

Amendment and Reply submitted Mar. 22, 2012, in U.S. Appl. No. 12/449,562, inventors Kuwano, K., et al., Int'l Filing Date of Feb. 15, 2008, U.S. Patent and Trademark Office, Alexandria, VA.

Office Action mailed Apr. 19, 2012, in U.S. Appl. No. 12/449,562, inventors Kuwano, K., et al., Int'l Filing Date of Feb. 15, 2008, U.S. Patent and Trademark Office, Alexandria, VA.

Amendment and Reply submitted Jun. 25, 2012, in U.S. Appl. No. 12/449,562, inventors Kuwano, K., el al., Int'l Filing Date Patent and Trademark Office Alexandria, VA.

Amendment and Reply submitted Aug. 1, 2012, in U.S. Appl. No. 12/449,562, inventors Kuwano, K., et al., Int'l Filing Date Feb. 15, 2008, U.S. Patent and Trademark Office, Alexandria, VA.

Office Action mailed Aug. 22, 2012, in U.S. Appl. No. 12/449,562, inventors Kuwano, K., et al., Int'l Filing Date of Feb. 15, 2008, U.S. Patent and Trademark Office, Alexandria, VA.

Amendment and Reply submitted Jan. 22, 2013, in U.S. Appl. No. 12/449,562, inventors Kuwano, K., et al., Int'l Filing Date of Feb. 15, 2008, U.S. Patent and Trademark Office, Alexandria, VA.

Office Action mailed Apr. 2, 2013, in U.S. Appl. No. 12/449,562, inventors Kuwano, K., et al., Int'l Filing Date of Feb. 15, 2008, U.S. Patent and Trademark Office, Alexandria, VA.

\* cited by examiner

SEQUENCE LISTING

<160> NUMBER OF SEQ ID NOS: 7

<210> SEQ ID NO 1
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 1

Lys Pro Asp Ala Ala Lys Lys Gly Val Val Lys Ala Glu Lys
1               5                   10

<210> SEQ ID NO 2
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 2

Lys Ser Gly Ala Glu Lys Lys Gly Pro Gly Arg Pro Thr Gly
1               5                   10

<210> SEQ ID NO 3
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 3

Cys Lys Pro Asp Ala Ala Lys Lys Gly Val Val Lys Ala Glu Lys
1               5                   10                  15

<210> SEQ ID NO 4
<211> LENGTH: 215
<212> TYPE: PRT
<213> ORGANISM: Sus scrofa

<400> SEQUENCE: 4

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys His Pro Tyr
    130                 135                 140

Glu Lys Lys Ala Ala Lys Leu Lys Glu Lys Tyr Glu Lys Asp Ile Ala
145                 150                 155                 160

```
Ala Tyr Arg Ala Lys Gly Lys Pro Asp Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Asp Glu Glu Glu
        195                 200                 205

Glu Glu Asp Asp Asp Asp Glu
        210             215

<210> SEQ ID NO 5
<211> LENGTH: 210
<212> TYPE: PRT
<213> ORGANISM: Sus scrofa

<400> SEQUENCE: 5

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Gly Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Glu Asp Glu Asp Glu Glu Glu Asp Glu Asp
        195                 200                 205

Glu Glu
    210

<210> SEQ ID NO 6
<211> LENGTH: 215
<212> TYPE: PRT
<213> ORGANISM: Homo sapiens

<400> SEQUENCE: 6

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45
```

```
Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
130                 135                 140

Glu Lys Lys Ala Glu Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Gly Glu Glu
                180                 185                 190

Asp Glu Glu Asp Glu Glu Glu Glu Asp Glu Asp Glu Asp
                195                 200                 205

Glu Glu Asp Asp Asp Asp Glu
210                 215

<210> SEQ ID NO 7
<211> LENGTH: 209
<212> TYPE: PRT
<213> ORGANISM: Homo sapiens

<400> SEQUENCE: 7

Met Gly Lys Gly Asp Pro Asn Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ser Ser Val Asn Phe Ala Glu Phe Ser Lys Lys Cys Ser Glu Arg
                 35                  40                  45

Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Lys Asp Pro Asn Ala Pro Lys
                 85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190
```

-continued

```
Glu Glu Glu Glu Glu Asp Glu Asp Glu Glu Glu Glu Asp Glu Asp Glu
        195                 200                 205
Glu
```

METHOD OF TREATING AMYKLOIDOSIS COMPRISING ADMINISTERING AN ANTI-HMGB-1 ANTIBODY

TECHNICAL FIELD

The present invention relates to agents for treating amyloidosis, which comprise an anti-HMGB-1 antibody as an active ingredient.

BACKGROUND ART

High mobility group box proteins (HMGBs) or high mobility group proteins (HMGs) were identified in 1964 as non-histone proteins abundant in the chromatin structure. High mobility group box proteins are ubiquitous proteins shared by all higher animals and plants, and their primary structures are remarkably highly conserved among species. HMGBs are known to be abundant not only in nucleus but also in cytoplasm. The biological function of HMGs is still poorly understood. However, based on the finding that HMGs unwind the DNA double helix structure upon binding to DNA, it is thought that HMGs function as a versatile transcription-enhancing factor or nucleosome-unwinding factor in transcription by optimizing DNA conformation to enhance transcriptional activity.

Several types of HMGBs have been identified, including, for example, high mobility group box protein 1 (HMGB-1 or HMG-1), high mobility group box protein 2 (HMGB-2 or HMG-2), high mobility group protein 3 (HMG-3), high mobility group protein 8 (HMG-8), high mobility group protein 17 (HMG-17), high mobility group protein I (HMG-I), high mobility group protein Y (HMG-Y), high mobility group protein I(Y) (HMG-I(Y)), and high mobility group protein I-C (HMG I-C).

Furthermore, the present inventors analyzed the amino acid homology using genetic information analysis software "GENETYX" (SOFTWARE DEVELOPMENT), and found that human HMGB-1 exhibits 98.6% and 99.1% homology to bovine and porcine HMGB-1, respectively. Furthermore, human HMGB-1 shows 81.2%, 72.3%, and 79.4% homology to human, bovine, and porcine HMGB-2, respectively.

In 1999, Wang et al. for the first time quantified serum (blood) HMGB-1 by Western blotting using the polyclonal antibody which was prepared using HMGB-1 itself as an immunogen, and demonstrated that HMGB-1 could be used as a sepsis marker. In addition, they showed that it is possible to predict the death and survival of sepsis patients through precise measurement of blood HMGB-1. Specifically, Wang et al. describe that the survival rate was significantly improved in the sepsis model mice administered with an antibody against HMGB-1 as compared to the untreated sepsis model mice. This suggests that HMGB-1 not only serves as a potential sepsis marker but may also be involved in sepsis as a causative agent. In other words, HMGB-1 may be a mediator of sepsis. Since no definitive therapy is available for sepsis to date, the discovery described above is very important (Non-patent Document 1).

Furthermore, various reported data demonstrate that HMGB-1 is also induced upon inflammation and is thought to trigger the secretion of substantial amounts of various cytokines (Non-patent Documents 2 to 4), supporting that HMGB-1 can be a target in therapy. This suggests the significant potential benefit of precisely quantifying blood HMGB-1 and inhibiting the function of HMGB-1, instead of simply detecting blood HMGB-1.

Furthermore, the present inventors have found that HMGB-2 is often detected in biological samples where HMGB-1 is detected (Non-patent Document 5). It has also been revealed that HMGB-2 does not have HMGB-1's mediator activity in diseases, even though HMGB-2 shares high homology with HMGB-1 (81.2%) (Non-patent Document 6). Therefore, it is very important to specifically measure or inhibit HMGB-1 without any HMGB-2 influence.

Antibodies are very useful tools in measuring blood HMGB-1 concentration and inhibiting the activity of HMGB-1 as a therapeutic target. However, it would be difficult to obtain antibodies exhibiting high affinity to HMGB-1, which specifically bind to HMGB-1 but not to HMGB-2.

The reason is not just the extremely high homology between HMGB-1 and HMGB-2. In general, when preparing an antibody against an antigen of interest, animals that are easy to care for (pigs, rabbits, goats, sheep, mice, rats, and the like) are immunized with the antigen of interest. Generally, all kinds of efforts are put into immunization, such as the use of adjuvants, to induce high-affinity antibodies. However, this may induce an inflammatory response, which in turn induces HMGB-1 in the animal body. Such treatments cause extremely high stress on the animals being immunized.

The very high inter-species homology of HMGB-1 also makes it difficult to obtain anti-human HMGB-1 antibodies. Specifically, the primary structures of pig, bovine, goat, sheep, mouse, and rat HMGB-1 differ from that of human HMGB-1 in only two or three residues at the amino acid level (Non-patent Document 7). Accordingly, when such an animal is immunized with human HMGB-1, high-affinity antibodies induced in the animal are absorbed by HMGB-1 induced in the immunized animal, and as a result, the antibodies obtained will have reduced quality and low affinity.

Moreover, individual difference among immunized animals is also an important factor when obtaining high-quality antibodies. The present inventors actually experienced that only one of five rabbits gave useful antibodies against HMGB-1 because of individual differences. This phenomenon is highly reproducible.

Documents of related prior arts for the present invention are described below.

Non-patent Document 1: H. Wang et al., Science, (1999) 285: 248-251
Non-patent Document 2: Andersson, U et al., J. Exp. Med, (2000) 192: 565-570
Non-patent Document 3: Scaffidi et al., Nature, (2002) 418: 191-195
Non-patent Document 4: Park et al., The Journal of Biological Chemistry, (2004) 279: 27
Non-patent Document 5: Shingo. Y., Clini Chem, (2003) 9: 1535-37
Non-patent Document 6: Ueno. H., Am J Respir Crit Car Med, 2004
Non-patent Document 7: L. Wen, Nucleic Acids Research, (1989) 17: 1197-1214
Non-patent Document 8: H. J. Lachmann and P. N. Hawkins, Curr Opin Pharmacol., (2006) 6: 214-20

DISCLOSURE OF THE INVENTION

Problems to be Solved by the Invention

An objective of the present invention is to provide novel agents for treating amyloidosis, which comprise an anti-HMGB-1 antibody as an active ingredient.

Means for Solving the Problems

The present inventors conducted dedicated studies and discovered that anti-HMGB-1 antibodies are effective for specific diseases, and thus completed the present invention. More specifically, the present invention comprises:

(1) an agent for treating amyloidosis, which comprises an anti-high mobility group box protein 1 (HMGB-1) antibody as an active ingredient;
(2) the therapeutic agent of (1), wherein the amyloidosis is a systemic amyloidosis;
(3) the therapeutic agent of (2), wherein the systemic amyloidosis is a secondary systemic amyloidosis;
(4) the therapeutic agent of any one of (1) to (3), wherein the anti-HMGB-1 antibody binds more strongly to HMGB-1 than to high mobility group box protein 2 (HMGB-2);
(5) the therapeutic agent of any one of (1) to (3), wherein the anti-HMGB-1 antibody does not bind to HMGB-2;
(6) the therapeutic agent of any one of (1) to (5), wherein the anti-HMGB-1 antibody recognizes a partial peptide comprising the amino acid sequence of SEQ ID NO: 1;
(7) a method for treating amyloidosis, which comprises the step of administering an anti-high mobility group box protein 1 (HMGB-1) antibody to a subject;
(8) the method of (7), wherein the amyloidosis is a systemic amyloidosis;
(9) the method of (8), wherein the systemic amyloidosis is a secondary systemic amyloidosis;
(10) the method of any one of (7) to (9), wherein the anti-HMGB-1 antibody binds more strongly to HMGB-1 than to high mobility group box protein 2 (HMGB-2);
(11) the method of any one of (7) to (9), wherein the anti-HMGB-1 antibody does not bind to HMGB-2;
(12) the method of any one of (7) to (11), wherein the anti-HMGB-1 antibody recognizes a partial peptide comprising the amino acid sequence of SEQ ID NO: 1;
(13) use of an anti-high mobility group box protein 1 (HMGB-1) antibody in manufacturing a therapeutic agent for amyloidosis;
(14) the use of (13), wherein the amyloidosis is a systemic amyloidosis;
(15) the use of (14), wherein the systemic amyloidosis is a secondary systemic amyloidosis;
(16) the use of any one of (13) to (15), wherein the anti-HMGB-1 antibody binds more strongly to HMGB-1 than to high mobility group box protein 2 (HMGB-2);
(17) the use of any one of (13) to (15), wherein the anti-HMGB-1 antibody does not bind to HMGB-2;
(18) the use of any one of (13) to (17), wherein the anti-HMGB-1 antibody recognizes a partial peptide comprising the amino acid sequence of SEQ ID NO: 1;
(19) an anti-high mobility group box protein 1 (HMGB-1) antibody used for amyloidosis treatment;
(20) the antibody of (19), wherein the amyloidosis is a systemic amyloidosis;
(21) the antibody of (20), wherein the systemic amyloidosis is a secondary systemic amyloidosis;
(22) the antibody of any one of (19) to (21), wherein the anti-HMGB-1 antibody binds more strongly to HMGB-1 than to high mobility group box protein 2 (HMGB-2);
(23) the antibody of any one of (19) to (21), wherein the anti-HMGB-1 antibody does not bind to HMGB-2; and
(24) the antibody of any one of (19) to (23), wherein the anti-HMGB-1 antibody recognizes a partial peptide comprising the amino acid sequence of SEQ ID NO: 1.

BRIEF DESCRIPTION OF THE DRAWINGS

The application file contains at least one drawing executed in color. Copies of this patent application publication with color drawings will be provided by the Office upon request and payment of the necessary fee.

MODE FOR CARRYING OUT THE INVENTION

Figure 1:
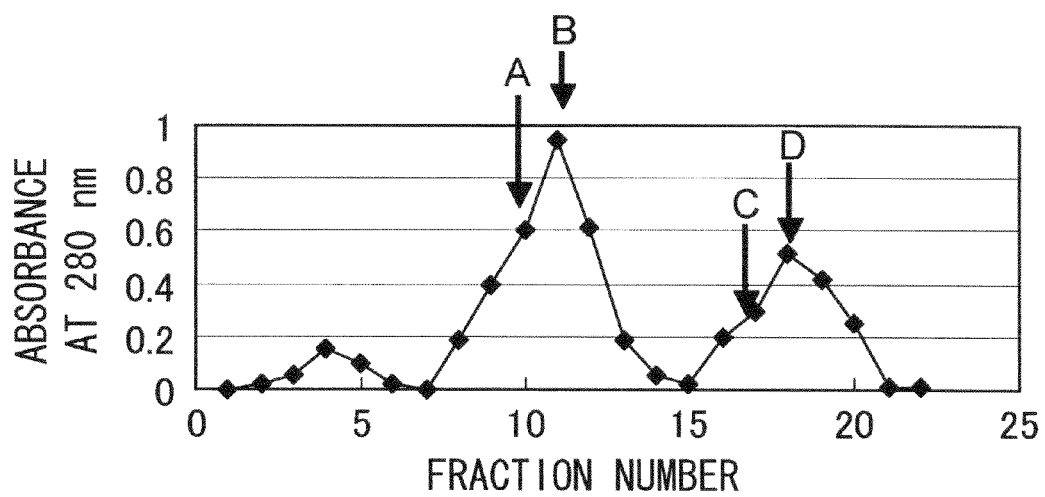
FIG. 1 shows the result obtained by monitoring the eluted fractions based on absorbance at 280 nm in the cation exchange chromatography when preparing HMGB-1 and HMGB-2 from pig thymus by the method of Sanders et al. The eluted fractions were subjected to 15% SDS-PAGE. The result showed that fractions A and B contained HMGB-1 while fractions C and D contained HMGB-2.

The present invention provides novel agents for treating amyloidosis. The present invention demonstrates that amyloidosis can be prevented or treated through administration of antibodies against HMGB-1.

Anti-HMGB-1 antibodies to be used in the present invention are not particularly limited as long as they bind to HMGB-1 and have the effect of treating amyloidosis. The origin (human, mouse, rat, rabbit, chicken, or such), type (polyclonal or monoclonal antibody), form (altered antibody, modified antibody, antibody fragment, minibody (low molecular weight antibody), or such), isotype (IgG, IgM, or such), and the like are not limited.

In a preferred embodiment, the antibodies of the present invention include antibodies that bind more strongly to HMGB-1 than to HMGB-2. Particularly preferred antibodies of the present invention include antibodies that bind more strongly to human HMGB-1 than to human HMGB-2. Herein, the antibodies that bind more strongly to HMGB-1 than to HMGB-2 refer to antibodies that have a greater binding activity for HMGB-1 than for HMGB-2. The difference in binding activity is not particularly limited, as long as the binding activity is greater for HMGB-1 than for HMGB-2. The binding activity is preferably two or more times greater, more preferably five or more times greater, and still more preferably ten or more times greater for HMGB-1 than for HMGB-2.

The binding of antibodies to HMGB-1 or HMGB-2 can be detected by methods known to those skilled in the art, for example, ELISA, BIACORE, Western blotting, or flow cytometry. Furthermore, the binding activity of antibodies can be determined by methods known to those skilled in the art, such as ELISA and BIACORE.

In another preferred embodiment, the antibodies of the present invention include antibodies that bind to HMGB-1 but not to HMGB-2. Particularly preferred antibodies of the present invention include antibodies that bind to human HMGB-1 but not to human HMGB-2. Herein, the phrase "not bind to HMGB-2" means that the binding between HMGB-2 and an anti-HMGB-1 antibody is substantially undetectable. Whether an anti-HMGB-1 antibody binds to HMGB-2 can be tested by conventional methods such as Western blotting and ELISA.

In another preferred embodiment, the antibodies of the present invention include antibodies that have an HMGB-1-neutralizing activity. Antibodies having the activity of neutralizing HMGB-1 can inhibit the binding between HMGB-1 and its receptor. The neutralizing activity of such an antibody can be tested by methods known to those skilled in the art, for example, ELISA and BIACORE.

Anti-HMGB-1 antibodies of the present invention can be produced as polyclonal or monoclonal antibodies by known methods. The antibodies can be prepared, for example, by immunizing an animal with the antigen.

HMGB-1 to be used as the immunogen is not particularly limited, and may be the whole protein constituting HMGB-1 or a partial peptide thereof. Alternatively, the HMGB-1 protein or a partial peptide thereof may be linked to other molecules, or a partial sequence (peptide) of HMGB-1 linked to an appropriate carrier may be used as the immunogen. If needed, cells expressing the antigen on their surface may also be used as the immunogen. Such cells may be natural cells (tumor cell line or the like) or cells modified by genetic recombination techniques to express the antigen molecule.

The antigens for immunizing animals include complete antigens with immunogenicity, and incomplete antigens (including haptens) without immunogenicity. Either of the two can be used to prepare antibodies to be used in the present invention.

The HMGB-1 protein and partial peptides thereof can be obtained by known methods, for example, methods for preparing HMGB-1 from human, porcine, or bovine thymus, human placenta, neutrophils, or cell lines such as HL-60 are known (Goodwin H et al., Biochem Biophy Acta (1975) 405: 280-91; Yoshida M et al., J Biochem (1980) 95: 117-24; Adachi Y et al., J Chromatogr (1992) 530: 39-46). Furthermore, a mixture of bovine HMGB-1 and HMGB-2 is commercially available from Wako Pure Chemical Industries. Thus, bovine HMGB-1 can be prepared from this product by purification.

Furthermore, the HMGB-1 genes of human, bovine, porcine, rabbit, mouse, rat, and such are known, and thus HMGB-1 can be prepared as an antigen based on the genetic information by genetic engineering techniques. For example, the amino acid and nucleotide sequences of human HMGB-1 are disclosed under GenBank Accession Nos. NP_002119 and NM_002128, respectively. HMGB-1 prepared from various animals by the methods described above can be used as an antigen (immunogen) to prepare antibodies for use in the present invention.

The preferred immunogens used for preparing the antibodies of the present invention include, for example, peptides comprising an amino acid sequence that is derived from HMGB-1 and exhibits only low homology to HMGB-2. The peptides to be used as an immunogen preferably comprise a highly hydrophilic amino acid sequence. The reason is that a more hydrophilic amino acid sequence is more likely to present on the surface of the HMGB-1 molecule, which increases the possibility that an antibody produced using it as the immunogen binds to HMGB-1. The hydrophilicity of each amino acid residue constituting the immunogen of the present invention can be estimated by the method of Hopp et al. (T. P. Hopp et al., Proc. Natl. Acad. Sci. USA (1981) 78: 3824-8), the method of Parker et al. (Parker et al., Biochemistry (1986) 25: 5425-32), etc.

Thus, particularly preferred immunogens used to prepare the antibodies to be used in the present invention include, for example, peptides comprising a highly hydrophilic amino acid sequence that is derived from HMGB-1 and exhibits only low homology to HMGB-2. Such peptides comprising a highly hydrophilic amino acid sequence that is derived from HMGB-1 and exhibits only low homology to HMGB-2 can be selected, for example, by methods as described in Example 1.

Specifically, the peptides comprising a highly hydrophilic amino acid sequence that is derived from HMGB-1 and exhibits only low homology to HMGB-2 include, for example, "Lys Pro Asp Ala Ala Lys Lys Gly Val Val Lys Ala Glu Lys" (SEQ ID NO: 1), spanning from amino acid residues 167 (lysine) to 180 (lysine) of human HMGB-1.

Animals are immunized with sensitizing antigens using known methods. Such conventional methods include intraperitoneal and subcutaneous injection of a sensitizing antigen into animals. Specifically, a sensitizing antigen is suspended and diluted with an appropriate amount of PBS, physiological saline, or such. If required, an appropriate amount of a conventional adjuvant, for example, Freund's complete adjuvant, is combined with the suspension, and the mixture is emulsified. Then, the emulsion is administered to animals several times at 4- to 21-day intervals. Appropriate carriers may be used when immunizing with the sensitizing antigen. After animals have been immunized and the level of antibody of interest in the sera is confirmed to be elevated, immune cells are collected from the animals to prepare hybridomas for obtaining monoclonal antibodies. The cells are then subjected to cell fusion. Animals to be immunized include mice, rats, hamsters, chickens, rhesus monkeys, and such.

Polyclonal or monoclonal antibodies that bind to HMGB-1 can be prepared, for example, by the methods described below.

Polyclonal Antibodies and Antisera

Polyclonal antibodies or antisera against HMGB-1 can be obtained by the procedure described below.

First, mammals (mice, rabbits, rats, sheep, goats, horses, and such), birds, or the like are immunized with the above-described immunogen or immunogen-carrier conjugate. Preferred animals to be immunized with HMGB-1 are birds such as chickens, when considering that: (1) immunization with HMGB-1 may cause severe inflammation and induce HMGB-1 in the blood of the immunized animals; and (2) as a result of the remarkably high inter-species homology of HMGB-1, the induced anti-HMGB-1 antibody is absorbed by inflammation-induced HMGB-1, and thus high affinity antibody of interest against HMGB-1 is reduced and low affinity antibody alone remains in the final antiserum preparation. The above-described phenomenon can be avoided when the objective is to attain an anti-human HMGB-1 antibody, since chicken HMBG-1 shows low homology to human HMGB-1 (76% homology in the amino acid sequence).

The immunization dose of the above-described immunogen or immunogen-carrier conjugate is determined depending on the animal species to be immunized, injection site for the immunization, etc. When mice (about five to ten weeks old) are immunized, the immunogen or immunogen-carrier conjugate is injected at a single dose of 0.1 μg to several mg per head, preferably 5 μg to 1 mg per head. Alternatively, when rabbits are immunized, the immunogen or immunogen-carrier conjugate is injected at a single dose of 10 μg to several tens of mg per each rabbit. When chickens are immunized, the immunogen or immunogen-carrier conjugate is injected at a single dose of 0.1 μg to several tens of mg per each chicken. It is preferred that the immunogen or immunogen-carrier conjugate is administered as a mixture with an adjuvant. The adjuvants include known adjuvants such as Freund's complete and incomplete adjuvants, aluminum hydroxide adjuvants, and pertussis adjuvants. The injection may be given subcutaneously (in the abdominal area, in the back, into footpads, or such), intravenously, intraperitoneally, or via other routes.

After the primary immunization, the above-described immunogen or immunogen-carrier conjugate is injected as a booster at two- to three-week intervals subcutaneously (in the abdominal area, in the back, into footpads, or such), intravenously, intraperitoneally, or via other routes. In this administration, it is also preferred that the above-described immunogen or immunogen-carrier conjugate is injected as a mixture with an adjuvant. After the primary immunization, the antibody titer in the serum of the immunized animal is repeatedly assessed by ELISA or the like. In general, when the antibody titer reaches a plateau, the whole blood is collected and the serum is separated to obtain an antiserum containing antibody to be used in the present invention.

The polyclonal antibody is purified from the antiserum by using a method or a combination of one or more methods of salting out such as with ammonium sulfate or sodium sulfate, ion exchange chromatography, gel filtration, affinity chromatography, etc.

The resulting polyclonal antibody contains both polyclonal antibodies, one that binds to HMGB-1 but not to HMGB-2, and another that binds to both HMGB-1 and HMGB-2. These antibodies can be separated into polyclonal antibodies that bind to HMGB-1 but not to HMGB-2, and polyclonal antibodies that bind to both HMGB-1 and HMGB-2, by affinity chromatography using a column immobilized with HMGB-2 as a ligand. Polyclonal antibodies that bind to both HMGB-1 and HMGB-2 are captured upon binding to the solid phase via the ligand (HMGB-2) in the column. Polyclonal antibodies that bind to HMGB-1 but not to HMGB-2 do not bind to the ligand (HMGB-2) in the column and thus pass through the column. Therefore, polyclonal antibodies that bind to human HMGB-1 but not to human HMGB-2 can be obtained by collecting the flow-through fractions.

When an animal is immunized with an immunogen-carrier conjugate, the resulting antiserum or polyclonal antibody also contains an antibody against the carrier. It is thus preferred to remove the antibody against the carrier. Antibodies against the carrier can be removed by adding the carrier to a solution of the obtained polyclonal antibody or antiserum and removing the formed aggregates, or by affinity chromatography using an insoluble solid phase immobilized with the carrier, or by other methods.

Monoclonal Antibodies

Monoclonal antibodies can be produced from antibody-producing cells such as hybridomas obtained by the cell fusion method of Koehler et al. (Koehler G et al., Nature (1975) 256: 495-7) or tumor cells transformed by viruses such as Epstein-Barr virus.

For example, monoclonal antibodies can be prepared by the cell fusion method with the procedure described below. First, mammals (such as mice, nude mice, and rats, for example, inbred mouse BALB/c), birds (such as chickens), or the like are immunized with the above-described immunogen or immunogen-carrier conjugate. The immunization dose of the above-described immunogen or immunogen-carrier conjugate is appropriately determined depending on the animal species to be immunized, injection site for the immunization, or the like. For example, the above-described immunogen or immunogen-carrier conjugate is preferably injected into mice at a single dose of 0.1 μg to 5 mg per head. Alternatively, the above-described immunogen or immunogen-carrier conjugate is preferably injected into chickens at a single dose of 0.1 μg to several tens of mg per chicken. The above-described immunogen or immunogen-carrier conjugate is preferably injected as a mixture with an adjuvant. The adjuvants include known adjuvants such as Freund's complete and incomplete adjuvants, aluminum hydroxide adjuvants, and pertussis adjuvants. The injection may be given subcutaneously (in the abdominal area, in the back, into footpads, or such), intravenously, or intraperitoneally, or via other routes.

After the primary immunization, the immunogen or immunogen-carrier conjugate described above is injected as a booster subcutaneously (in the abdominal area, in the back, into footpads, or such), intravenously, or intraperitoneally, or via other routes, at one- to two-week intervals. In general, two to six booster injections are carried out. In this case, it is preferred that the above-described immunogen or immunogen-carrier conjugate is also injected as a mixture with an adjuvant.

After the primary immunization, the antibody titer in the serum of the immunized animal is repeatedly assessed by ELISA or the like. In general, when the antibody titer reaches a plateau, the above-described immunogen or immunogen-carrier conjugate is dissolved, for example, in PBS or physiological saline (aqueous solution of 0.9% sodium chloride), and injected intravenously or intraperitoneally for the final immunization. Three or five days after the final immunization, cells having the ability to produce antibody, such as spleen cells, lymph node cells, or peripheral lymphocytes, are harvested from the immunized animal.

The cells that have the ability to produce antibody from the immunized animal (mouse, nude mouse, rat, or such) are fused with myeloma cells. Basically, the cell fusion between the immune cells and myeloma cells can be performed by known methods, for example, according to the method of Kohler and Milstein (Kohler and Milstein, Methods Enzymol (1981) 73: 3-46).

More specifically, cell fusion can be carried out, for example, using a cell fusion-enhancing agent. For example, polyethylene glycol (PEG), hemagglutinating virus of Japan (HVJ), or such can be used as the fusion-enhancing agent. If required, an adjuvant such as dimethylsulfoxide can be added to improve fusion efficiency. The ratio of immune cells to myeloma cells can be appropriately determined. In general, for example, it is preferable to use one to ten immune cells for each myeloma cell. Culture media used for these cells include, for example, RPMI1640 and MEM, which are suitable for growing myeloma cell lines. Culture media generally used for these types of cell cultures can also be suitably used. Furthermore, serum supplements such as fetal calf serum (FCS) may be added to culture media. Cell fusion can be carried out by the following procedure: mixing immune cells well with a specified quantity of myeloma cells in a culture medium; pre-warming a PEG (for example, average molecular weight of about 1,000 to 6,000) solution to about 37° C.; adding the PEG solution at a concentration of 30% to 60% (w/v); and then mixing the combined solution to generate fused cells (hybridomas) of interest. Next, to remove cell fusion-enhancing agents and the like, which are unfavorable to hybridoma growth, the following steps are repeated: adding an appropriate culture medium sequentially; centrifuging the mixture; and removing the supernatant. Hybridoma selection can be achieved by culturing the generated hybridomas in a conventional selection medium, for example, HAT medium (a culture medium containing hypoxanthine, aminopterin, and thymidine). Culture is continued using the above-described HAT medium for a sufficient period of time (typically, several days to several weeks) to kill cells (non-fused cells) other than the hybridomas of interest. The hybridomas are then screened and hybridomas producing desired antibodies are cloned into single clones according to conventional limiting dilution methods or colony methods using methylcellulose-containing semi-solid medium.

Herein, preferable immune cells include, particularly, spleen cells. In general, mammalian myeloma cells are used as parental cells for fusion with the immune cells. Various myeloma cell lines are known, and any of them can be used. Those preferably used include, for example, P3 (P3x63Ag8.653) (J. Immunol. (1979) 123: 1548-50), P3x63Ag8U.1 (Curr. Topics Microbiol. Immunol. (1978) 81: 1-7), NS-1 (Kohler and Milstein, Eur. J. Immunol. (1976) 6: 511-9), MPC-11 (Margulies et al., Cell (1976) 8: 405-15), SP2/0 (Shulman et al., Nature (1978) 276: 269-70), F0 (deSt. Groth et al., J. Immunol. Methods (1980) 35: 1-21), S194 (Trowbridge, J. Exp. Med. (1978) 148: 313-23), and R210 (Galfre et al., Nature (1979) 277: 131-3).

The supernatants of hybridomas obtained as described above can be assayed by immunoassay methods such as ELISA and Western blotting using the above-described immunogen, immunogen-carrier conjugate, human HMGB-1, or the like, to select hybridomas that produce human HMGB-1-binding antibody or such. Furthermore, the culture supernatants of hybridomas can be assayed by immunoassay methods such as ELISA and Western blotting using human HMGB-2 or such to select hybridomas producing an antibody that binds more strongly to human HMGB-1 than to human HMGB-2, an antibody that binds to human HMGB-1 but not to human HMGB-2, or such. Cell lines producing particularly preferred antibodies (monoclonal antibodies) to be used in the present invention, specifically antibodies (monoclonal antibodies) that bind to human HMGB-1 but not to human HMGB-2, can be isolated by using a combination of those two types of hybridoma selection methods and known cloning methods such as the limiting dilution method and the colony method using methylcellulose-containing semi-solid medium. Monoclonal antibody-producing hybridomas prepared by the procedure described above can be passaged in conventional culture media and stored in liquid nitrogen for a long term.

Methods for obtaining monoclonal antibodies from hybridomas include a method of obtaining monoclonal antibodies as culture supernatants of hybridomas cultured by conventional methods. Alternatively, a method can be adopted which comprises administering hybridomas to an abdominal cavity of an animal compatible with the hybridomas, allowing the cells to grow, and obtaining monoclonal antibodies from ascites of the animal. In this case, it is better to administer pristine beforehand in the abdominal cavity of the animal for stimulation. The former method is suitable for preparing high purity antibodies, and the latter is suitable for large scale production of antibodies.

Serum-free media, low-serum media, media containing antibody-depleted serum may be used when an antibody is prepared by culturing cells of a cell line producing the monoclonal antibody. DMEM, RPMI1640 medium, ASF 103 medium, and the like can be preferably used due to the convenience of antibody purification.

Alternatively, instead of obtaining hybridomas by immunizing nonhuman animals with an antigen by the procedures described above, hybridomas producing the desired human antibody can be obtained by sensitizing human lymphocytes with an antigen in vitro and fusing the sensitized lymphocytes with human myeloma cells that are capable of perpetual division (see Japanese Patent Application Kokoku Publication No. (JP-B) H1-59878 (examined, approved Japanese patent application published for opposition). Alternatively, hybridomas producing the desired human antibody may be obtained by administering an antigen to transgenic animals that have the entire repertoire or a part of human antibody genes to produce antibody-producing cells, and then immortalizing them (see WO 94/25585, WO 93/12227, WO92/03918, and WO 94/02602).

Antibody Fragments

The anti-HMGB-1 antibodies used in the present invention may be an antibody fragment or modified antibody as long as they bind to HMGB-1 and have the effect of treating amyloidosis. Such antibody fragments include Fv, Fab, Fab', F(ab')$_2$, diabody (Db), linear antibody, and single-chain antibody (herein also referred to as scFv) molecules. The "Fv" fragment is a minimal antibody fragment containing the complete antigen recognition and binding sites. "Fv" is a dimer ($V_H$-$V_L$ dimer) composed of one heavy (H) chain variable region ($V_H$) and one light (L) chain variable region ($V_L$) bound strongly by non-covalent bonding. An antigen binding site is formed on the surface of the $V_H$-$V_L$ dimer through interactions between the three complementarity determining regions (CDRs) of each variable region. Six CDRs form the antigen binding site of an antibody. However, even one variable region (i.e., half of an Fv containing only three antigen-specific CDRs) has the ability to recognize and bind to an antigen, although its affinity is lower than that of the complete binding site. Thus, fragments containing only one variable region or CDR, and half part of Fv containing only three CDRs can also be used in the present invention, as long as they bind to HMGB-1 and have the effect of treating amyloidosis.

An Fab fragment (also referred to as F(ab)) further contains an L-chain constant region and an H-chain constant region (CH1). An Fab' fragment (also referred to as F(ab')) differs from an Fab fragment in that it has several additional residues derived from the carboxyl end of the H-chain CH1 region which contains one or more cysteines from the hinge domain of an antibody. Fab'-SH fragment (also referred to as F(ab')-SH) refers to an Fab' fragment that has free thiol-group in one or more cysteine residues in the constant region. F(ab')$_2$ fragment is an antibody fragment in which two molecules of Fab'-SH fragment are linked together via disulfide bond. Specific methods for producing such antibody fragments include: methods in which the antibody fragments are produced by treating whole antibody molecules with enzymes such as papain or pepsin; and methods in which a gene encoding an antibody fragment is constructed and inserted into an expression vector, and then expressed in appropriate host cells (for example, Co M S et al., J Immunol (1994) 152: 2968-76). Other antibody fragments known to those skilled in the art include antibody fragments with chemical crosslinkages. These antibodies may also be used in the present invention.

A diabody refers to a bivalent antibody fragment constructed by gene recombination method (Holliger P et al., Proc. Natl. Acad. Sci. USA (1993) 90: 6444-6448; EP 404, 097; WO 93/11161 and such). Diabodies are dimers composed of two polypeptide chains, and in each polypeptide chain, an antibody-derived L-chain variable region ($V_L$) and an H-chain variable region ($V_H$) are linked via a linker short enough, for example, a linker of about five amino acids, within the same chain that they cannot bind to each other. The $V_L$ and $V_H$ domains encoded by a same polypeptide chain form a dimer because the linker between $V_L$ and $V_H$ is too short to form a single-chain variable region fragment. Therefore, a diabody contains two antigen-binding sites.

Single-chain antibodies and scFv antibody fragments contain antibody $V_H$ and $V_L$ regions, and these regions exist within a single polypeptide chain. In general, Fv polypeptides further contain a polypeptide linker between $V_H$ and $V_L$ regions. Thus, scFv is able to form a structure required for antigen binding (Huston J S et al., Proc. Natl. Acad. Sci. USA (1988) 85: 5879-83; as a review on scFv, see Pluckthun "The Pharmacology of Monoclonal Antibodies" Vol. 113 (Rosenburg and Moore ed. (Springer Verlag, New York) pp. 269-315, 1994)). The linker of the present invention is not particularly limited, as long as it does not completely inhibit the expression and activity of antibody variable regions linked at its two ends.

scFv-encoding DNAs can be prepared, for example, by the procedure described below:

(1) DNAs encoding a target partial amino acid sequence of an above-described antibody are amplified by PCR using DNA encoding the H chain or H chain V region, and DNA encoding the L chain or L chain V region as templates, and primer pairs at the ends thereof; and (2) DNA is then amplified using in combination a peptide linker-encoding DNA and primer pairs designed so that the respective H and L chains are linked to the ends of the linker.

Once the scFv-encoding DNA is constructed, expression vectors carrying the DNA and hosts transformed with the expression vectors can be obtained by conventional methods. Furthermore, the scFv can be prepared by conventional methods using the hosts.

Furthermore, if needed, the antibodies to be used in the present invention may be bispecific antibodies. IgG-type bispecific antibodies can be secreted from hybrid hybridomas (quadromas), which are generated by fusing two types of IgG antibody-producing hybridomas (Milstein C et al., Nature (1983) 305: 537-540). Alternatively, bispecific antibodies can be secreted by introducing into cells genes of the L chains and H chains constituting two types of IgGs of interest and coexpressing a total of four genes. If needed, IgG with a heterologous combination of H chains can be preferentially secreted by introducing appropriate amino acid substitutions into the H-chain CH3 region (Ridgway J B et al., Protein Engineering (1996) 9: 617-621; Merchant A M et al., Nature Biotechnology (1998) 16: 677-681).

Alternatively, bispecific antibodies can be prepared by chemically crosslinking Fab'. Bispecific F(ab')$_2$ can be prepared by crosslinking two Fab' derived from different antibodies, for example, by maleimidating Fab' prepared from one antibody with ortho-phenylenedimaleimide (o-PDM) and then reacting it with Fab' prepared from the other antibody (Keler T et al., Cancer Res. (1997) 57: 4008-4014). Furthermore, there are known methods for chemically linking antibody fragments such as Fab'-thionitrobenzoic acid (TNB) derivatives and Fab'-thiol (SH) (Brennan M et al., Science (1985) 229: 81-83).

Leucine zippers, such as those derived from Fos and Jun, may be used instead of chemical crosslinks. This takes advantage of the fact that Fos and Jun prefer to form heterodimers although they form homodimers too. Fab' attached to Fos-derived leucine zipper and Fab' attached to Jun-derived leucine zipper are expressed. Bispecific F(ab')$_2$ can be prepared by mixing and reacting monomers of Fab'-Fos and Fab'-Jun reduced under a mild condition (Kostelny S A et al., J. Immunol (1992) 148: 1547-53). This method is not limited to Fab' and can also be applied when linking scFv, Fv, or such.

Diabodies can also be prepared to have bispecificity. Bispecific diabodies are heterodimers of two cross-over scFv fragments. Specifically, bispecific diabodies can be obtained by preparing a heterodimer composed of $V_H$(A)-$V_L$(B) and $V_H$(B)-$V_L$(A), both of which are produced by linking $V_H$ and $V_L$ derived from two types of antibodies A and B, via a relatively short linker of about five residues (Holliger P et al., Proc. Natl. Acad. Sci. USA (1993) 90: 6444-6448).

Alternatively, the target configuration can be enhanced by linking two types of scFv via a relatively long, flexible linker of about 15 residues (single-chain diabody; Kipriyanov S M et al., J Mol Biol. (1999) 293: 41-56) or by appropriate amino acid substitution (knobs-into-holes: Zhu Z et al., Protein Sci. (1997) 6: 781-788). sc (Fv)$_2$ prepared by linking two types of scFv via a relatively long, flexible linker of about 15 residues can also be bispecific antibodies (Mallender W D et al., J Biol Chem. (1994) 269: 199-206).

Recombinant Antibodies

Antibodies to be used in the present invention can also be prepared as recombinant antibodies by using genetic recombination techniques to clone antibody genes from hybridomas, insert the genes into appropriate vectors, and introduce the resulting vectors into hosts (see, for example, Vandamme et al., Eur. J. Biochem. (1990) 192: 767-75). Specifically, an mRNA is first prepared from hybridomas producing an antibody of interest. Total RNA is prepared from antibody-producing spleen cells by known methods, for example, guanidine-ultracentrifugation methods (Chirgwin et al., Biochemistry (1979) 18: 5294-9) and AGPC methods (Chomczynski et al., Anal. Biochem. (1987) 162: 156-9), and then a mRNA is prepared using an mRNA Purification Kit (Pharmacia) or such. Alternatively, it is possible to directly prepare just the mRNA without preparing total RNA by using the QuickPrep mRNA Purification Kit (Pharmacia). Then, cDNA for the antibody V region is synthesized from the obtained mRNA using reverse transcriptase. cDNA synthesis can be carried out using the AMV Reverse Transcriptase First-strand cDNA Synthesis Kit (Seikagaku Co.) or such. Alternatively, cDNA can be synthesized and amplified by PCR-based 5'-RACE (Frohman et al., Proc. Natl. Acad. Sci. USA (1988) 85: 8998-9002; Belyaysky et al., Nucleic Acids Res. (1989) 17: 2919-32) using a 5'-Ampli FINDER RACE Kit (Clontech) or such. For example, cDNAs of the L-chain and H-chain variable regions ($V_L$, $V_H$) are amplified by RT-PCR using primers corresponding to sites adjacent to the variable regions, and then collected. It is possible to use as a primer the primers corresponding to the CDRs, primers corresponding to the frameworks which are less diverse than the CDRs, and primers corresponding to the signal sequence and CH1 or L-chain constant region ($C_L$). Then, a DNA fragment of interest is purified from the obtained PCR product and ligated with a vector DNA to prepare a recombinant vector. The recombinant vector is then introduced into a host cell such as E. coli, and colonies of transformed cells are selected. The desired recombinant antibody can be produced by culturing the prepared cells. If required, the nucleotide sequence of a gene encoding the antibody of interest is determined by known methods, for example, dideoxynucleotide methods.

The obtained DNA which encodes the V region of the antibody obtained as above can also be inserted into an expression vector that carries a DNA encoding a desired antibody constant region (C region). The expression vector has an expression regulatory region, for example, an enhancer and promoter. The antibody DNA which is used in the therapeutic agent of the present invention is incorporated into the expression vector so that the antibody is expressed under the regulation of the expression regulatory region. Then, the desired antibody molecule is expressed and prepared by transforming appropriate host cells with the expression vector.

To express an antibody gene, DNAs encoding an antibody heavy chain (H chain) and light chain (L chain) may be separately inserted into different expression vectors and host cells may be co-transformed with these vectors, or host cells may be transformed with a single expression vector carrying both an H-chain-encoding DNA and an L-chain-encoding DNA (see WO 94/11523).

Human Antibodies and Humanized Antibodies

There is no limitation on the origin of antibodies of the present invention. The antibodies include chicken, mouse, and rat antibodies. However, when administered to human, the antibodies are preferably human or humanized antibodies. Methods for preparing human antibodies are already known. For example, human antibodies of interest can be obtained by using an antigen of interest to immunize transgenic animals that have the entire or a fraction of repertoire of human antibody genes (see WO 93/12227, WO 92/03918, WO 94/02602, WO 94/25585, WO 96/34096, and WO 96/33735).

Recombinant antibodies to be used in the present invention may be altered antibodies prepared by using genetic engineering techniques to reduce heteroantigenicity against humans or for other purposes. Such altered antibodies include chimeric antibodies and humanized antibodies comprising a human antibody constant region. Such genetically altered antibodies can be produced by known methods. Specifically, for example, chimeric antibodies comprise the variable regions of H and L chains of antibodies from an immunized animal, and the constant regions of H and L chains of a human antibody. Chimeric antibodies can be obtained by ligating DNAs that encode the variable regions of an antibody derived from an immunized animal with DNAs encoding the constant regions of a human antibody, inserting the ligated DNA into an expression vector, and then introducing the construct into a host.

Humanized antibodies are altered antibodies that are also referred to as "reshaped human antibodies". Humanized antibodies can be constructed by grafting the CDR of an antibody derived from an immunized animal to the CDR of a human antibody. Conventional gene recombination techniques are also available. Specifically, a DNA sequence is designed such that the framework region (FR) of a human antibody is linked with a CDR of a mouse antibody, and divided into several oligonucleotides having overlapping portions at their ends. The oligonucleotides are synthesized and assembled by PCR into the designed DNA sequence. The assembled DNA is ligated to DNA encoding a human antibody constant region, and then inserted into an expression vector. The vector construct is introduced into host cells to produce a humanized antibody (see EP 239400; WO 96/02576).

The human antibody FR to be ligated with CDR is selected so that the CDR of a resulting humanized antibody forms an appropriate antigen-binding domain. If required, some amino acids in the FR of the humanized antibody variable region may be replaced with other amino acids so that the CDR of the humanized antibody forms a suitable antigen-binding domain (Sato K et al., Cancer Res. (1993) 53: 851-6). Alternatively, the FR of the antibody variable region may be replaced with any of other various human antibody FRs (see WO 99/51743).

Antibodies with Altered Amino Acids

The antibodies to be used in the present invention also include altered antibodies having an amino acid sequence with an amino acid substitution, deletion, addition, and/or insertion in the amino acid sequence of an antibody prepared as described above. The amino acid sequences can be altered by known methods. It is preferred that the antibodies altered by amino acid substitution, deletion, addition, and/or insertion retain the same activity as the original antibodies.

Herein, "the same activity" means the same biological or biochemical activity as the original antibodies. Specifically, the biological or biochemical activity includes, for example, the binding activity and neutralizing activity.

In general, antibodies retaining the same activity as the original antibodies have high homology to the original antibodies. Herein, high homology typically means an amino acid identity of at least 50% or more, preferably 75% or more, more preferably 85% or more, and still more preferably 95% or more. Polypeptide homology can be determined using algorithms described in references, for example, the report of Wilbur and Lipman (Wilbur and Lipman, Proc. Natl. Acad. Sci. USA (1983) 80: 726-30).

The antibodies of the present invention include such altered antibodies comprising an amino acid substitution, deletion, addition, and/or insertion.

Modified Antibodies

The antibodies of the present invention also include modified antibodies. Such modified antibodies include, for example, antibodies conjugated with various molecules such as polyethylene glycol (PEG). There is no limitation as to the type of substance conjugated with modified antibodies used as a therapeutic agent of the present invention. Antibodies may be modified for various purposes, for example, to stabilize them, or to enhance their binding activity. Modified antibodies can be obtained by chemically modifying the obtained antibodies. Such methods have already been established in this field.

Expression and Production of Antibodies

Antibodies can be prepared by expressing the constructed antibody genes using known methods. When mammalian cells are used, the antibody genes can be expressed using expression vectors carrying a DNA in which an antibody gene to be expressed is operably linked to a conventional useful promoter/enhancer and a poly A signal downstream of the 3' side of the antibody gene. Such promoters/enhancers include, for example, the human cytomegalovirus immediate early promoter/enhancer. Other available promoters/enhancers include viral promoters/enhancers such as those from retrovirus, polyoma virus, adenovirus, and simian virus 40 (SV40); and promoters/enhancers derived from mammalian cells, such as human elongation factor 1α promoter/enhancer. For example, when the SV40 promoter/enhancer is used, the antibody genes can be easily expressed by the method of Mulling et al. (Mulling R C et al., Nature (1979) 277: 108-14). Alternatively, when the human elongation factor 1 a promoter/enhancer is used, the antibody genes can be easily expressed by the method of Mizushima (Mizushima, Nucleic Acids Res (1990) 18: 5322). When $E.\ coli$ is used, the antibody genes can be expressed by using expression vectors carrying a DNA in which an antibody gene to be expressed is operably linked to a conventional useful promoter and a signal sequence for antibody secretion. Such promoters include, for example, the lacZ promoter and the araB promoter.

When the lacZ promoter is used, for example, it is possible to use the method of Ward et al. (Ward E S et al., Nature (1989) 341: 544-6). Alternatively, when the araB promoter is used, it is possible to use the method of Better et al. (Bette M et al., Science (1988) 240: 1041-3). When the antibodies are produced into the periplasm of $E.\ coli$, the pel B signal sequence (Lei S P et al., J Bacteriol (1987) 169: 4379-83) may be used as a signal sequence for antibody secretion. The antibodies produced into the periplasm are isolated, and then used after appropriately refolding the antibody structure (WO 96/30394).

It is possible to use the replication origins derived from bovine papilloma viruses, polyoma viruses, adenoviruses, and simian viruses (SV40). In addition, the expression vectors may comprise the aminoglycoside phosphotransferase gene, thymidine kinase gene, $E.\ coli$ xanthine-guanine phosphoribosyltransferase gene, dihydrofolate reductase gene, or the like. These genes are used as a selection marker to increase the gene copy number in the host cell system.

Any production system may be used to produce antibodies to be used in the present invention. In vitro and in vivo production systems are available as antibody production systems. Such in vitro production system includes those using eukaryotic or prokaryotic cells. The production system using eukaryotic cells include those using animal, plant, or fungal cells. Animal cells include: (a) mammalian cells, for example, CHO and COS; (b) amphibian cells such as $Xenopus\ laevis$ oocytes, and (c) insect cells, for example, Sf9 and Sf21. Plant cells include, for example, cells derived from the genus $Nicotiana$. Calluses can be cultured from these cells. Fungal cells include: (a) yeast cells, for example, cells of the genus $Saccharomyces$; and (b) cells of filamentous fungi, for example, the genus $Aspergillus$. Bacterial cells can be used in the prokaryotic production systems. The bacterial cells include $E.\ coli$ and $Bacillus\ subtilis$. The antibodies can be obtained by introducing antibody genes of interest into these cells by transformation, and culturing the transformed cells in vitro. The culture can be carried out according to known methods. When mammalian cells are used as a host, for example, DMEM, MEM, and RPMI1640 may be used as a culture medium, which may be supplemented with serum supplements such as fetal bovine serum. It is also possible to use serum-free culture media. Alternatively, cells introduced with an antibody gene may be transplanted into the peritoneal cavity of an animal to produce the antibody in vivo. In vivo production system includes those using animals or plants. When animals are used, the production system includes, for example, those using mammals or insects. The mammals include goats, pigs, sheep, mice, and bovines.

Alternatively, the mammals may be transgenic animals. For example, a fusion gene is constructed by inserting an antibody gene into a gene encoding a protein specifically produced in milk, such as the goat β-casein gene. A DNA fragment comprising the fusion gene inserted with the antibody gene is injected into goat embryos, which are then introduced back into female goats. The antibody of interest can be obtained from milk produced by the transgenic goats, which are born from goats that received the embryos, or from their offspring. Appropriate hormones may be administered to increase the volume of milk containing the antibody of interest produced by the transgenic goats. For insects, it is possible to use silkworms. Baculoviruses carrying an antibody gene of interest may be used to infect silkworms, and the antibody of interest can be obtained from the body fluids of the silkworms (Maeda S et al., Nature (1985) 315: 592-4). Alternatively, it is possible to use plants, for example, tobacco to produce antibodies. When tobacco is used, a polynucleotide encoding an antibody of interest is inserted into a plant expression vector, for example, pMON530, and then the vector is introduced into bacteria, such as $Agrobacterium\ tumefaciens$. The bacteria are then used to infect tobacco such as $Nicotiana\ tabacum$, and the desired antibody can be obtained from the leaves (Ma et al., Eur J Immunol (1994) 24: 131-8).

Purification of Antibodies

The antibodies obtained by hybridoma culture and proliferation or gene recombination described above can be purified to homogeneity. Antibodies can be separated and purified by conventional methods for protein separation and purification. For example, antibodies can be separated and purified by appropriately selecting or combining methods that include, but are not limited to, chromatographic columns for affinity chromatography or such; filtration; ultrafiltration; salting out by ammonium sulfate, sodium sulfate, or such; dialysis; SDS-polyacrylamide gel electrophoresis; and isoelectric focusing (Antibodies: A Laboratory Manual. Ed Harlow and David Lane, Cold Spring Harbor Laboratory, 1988). Columns for affinity chromatography include protein A columns, protein G columns, and protein L columns.

The anti-HMGB-1 antibodies to be used in the present invention can be selected by assessing the reactivity to human HMGB-1, for example, using ELISA.

Agents for Treating/Preventing Amyloidosis

The present invention provides agents for treating amyloidosis, which comprise an anti-HMGB-1 antibody as an active ingredient. Herein, amyloidosis refers to diseases with amyloid deposition in various tissues. The diseases are categorized into amyloidosis secondary to tuberculosis, myeloma, or such; cryptogenic amyloidosis; hereditary amyloidosis; and so on, and develop various symptoms depending on the distribution, site, or the like of deposition. The therapeutic agents of the present invention comprising an anti-HMGB-1 antibody are suitable for treating and/or preventing amyloid deposition, in particular, in systemic amyloidosis. Furthermore, the therapeutic agents of the present invention are suitable for treating and/or preventing amyloid deposition in secondary systemic amyloidosis.

Therapeutic agents comprising anti-HMGB-1 antibodies of the present invention as an active ingredient may be formulated by mixing with suitable pharmaceutically acceptable carriers and media that are non-reactive to the antibodies, as necessary. Such carriers and media include, for example, sterilized water, saline, stabilizers, vehicles, antioxidants (ascorbic acid and such), buffers (phosphate, citrate, other organic acids and such), preservatives, detergents (PEG, Tween, and such), chelating agents (EDTA and such), and binding agents. Alternatively, the pharmaceutical compositions may comprise other low-molecular-weight polypeptides, proteins such as serum albumin, gelatin and immunoglobulins, amino acids such as glycine, glutamine, asparagine, arginine, and lysine, carbohydrates and sugars such as polysaccharides and monosaccharides, and sugar alcohols such as mannitol and sorbitol. When prepared as an aqueous solution for injection, it is possible to use saline and isotonic solutions containing glucose and other adjunctive agents such as D-sorbitol, D-mannose, D-mannitol, and sodium chloride. In addition, appropriate solubilizers such as alcohols (ethanol and such), polyalcohols (propylene glycol, PEG, and such), and non-ionic detergents (polysorbate 80, HCO-50, and such) may be used in combination.

Therapeutic agents of the present invention may comprise two or more types of anti-HMGB-1 antibodies as long as the functions of the antibodies are not inhibited. Furthermore, therapeutic agents of the present invention may be used in combination with other therapeutic agents for treating amyloidosis, if needed.

If necessary, therapeutic agents of the present invention may be encapsulated in microcapsules (microcapsules of hydroxymethylcellulose, gelatin, poly[methylmethacrylate], and the like). Alternatively, therapeutic agents of the present invention may be made into colloidal drug delivery systems (liposomes, albumin microsphere, microemulsion, nanoparticles, nanocapsules and the like; see "Remington's Pharmaceutical Science 16th edition", Oslo Ed. 1980), if necessary. Furthermore, methods for preparing agents as sustained-release agents are also known, and these can be applied in the therapeutic agents of the present invention (Langer et al., J. Biomed. Mater. Res. (1981) 15: 267-277; Langer, Chemtech. (1982) 12: 98-105; U.S. Pat. No. 3,773,919; EP 58,481; Sidman et al., Biopolymers (1983) 22: 547-556; EP 133,988).

The dose of a therapeutic agent of the present invention is ultimately properly determined by physicians, in consideration of the type of dosage form, administration method, patient's age, weight, symptoms, disease type and progression, and other factors. Typically, antibody content of 0.1 to 10,000 mg/day can be administered to an adult once or several times. More preferably, the dose ranges from 5 to 5,000 mg/day, and even more preferably from 50 to 2,000 mg/day. The dose varies depending on the patient's weight and age, administration method, and the like; however, the dose can be properly selected by those skilled in the art. The period of administration is preferably properly determined according to the course of treatment and the like for each patient. The administration route is not particularly limited, and may be intravenous or subcutaneous administration.

In addition, genes encoding antibodies to be used in the therapeutic agents of the present invention may be integrated into gene therapy vectors and used in gene therapy. Methods for administering the antibody-encoding genes include direct injection of naked plasmids, as well as liposome packaging, formation and administration of various viral vectors such as retrovirus vectors, adenovirus vectors, vaccinia virus vectors, poxvirus vectors, adenovirus related vectors, and HVJ vectors (see Adolph "Virus Genome Methods", CRC Press, Florida (1996)), or by coating onto carrier beads such as colloidal gold particles (for example, WO93/17706). However, any method can be used for administration as long as the antibodies are expressed in vivo and exercise their function. Preferably, a sufficient dose is administered by a suitable parenteral route, such as intravenous, intraperitoneal, subcutaneous, or intracutaneous injection, or injection into adipose tissues or mammary glands, inhalation or intramuscular injection or infusion, gas-induced particle bombardment (using electron guns and such), or through the mucosa, for example, by nose drops. Alternatively, genes encoding the antibodies of the present invention may be introduced, for example, into blood cells and bone marrow-derived cells ex vivo using liposome transfection, particle bombardment (U.S. Pat. No. 4,945,050), or viral infection, and then the cells can be administered to patients.

Furthermore, the present invention provides methods for treating amyloidosis, which comprise the step of administering a therapeutic agent of the present invention. The antibodies and therapeutic agents thereof can be administered, for example, by the methods described above. Furthermore, the present invention relates to the use of anti-HMGB-1 antibodies in producing the therapeutic agents of the present invention. In addition, the present invention provides kits that comprise at least a therapeutic agent of the present invention and are used for conducting the methods described above. The kits may additionally comprise syringes, needles, pharmaceutically acceptable media, alcohol pads, adhesive plasters, instruction manuals containing a description of how to use the kits, and others.

All prior art documents cited in the specification are incorporated herein by reference.

EXAMPLES

Hereinbelow, the present invention will be specifically described with reference to the Examples, but it is not to be construed as being limited thereto.

Example 1

Selection of Highly Hydrophilic Amino Acid Sequences in the Amino Acid Sequence of Human HMGB-1, which Exhibit Low Homology to Human HMGB-2

Highly hydrophilic amino acid sequences that exhibit low homology to human HMGB-2 were selected from the amino acid sequence of human HMGB-1.

(1) The amino acid sequence of human HMGB-1 (SEQ ID NO: 6) is shown above as the data of Wen et al. (Wen et al., Nucleic Acids Res. (1989) 17: 1197-214).
(2) The hydrophilicity of each amino acid residue in the amino acid sequence of human HMGB-1 was estimated by the method of Hopp et al. (T. P., Hopp et al., Proc. Natl. Acad. Sci. USA (1981) 78: 3824-8).
(3) Next, highly hydrophilic amino acid sequences from the amino acid sequence of human HMGB-1 were compared with the amino acid sequence of human HMGB-2 (M. Yoshida et al., J. Biol. Chem. (1992) 267: 6641-5). Then, some amino acid sequences exhibiting low homology to human HMGB-2 were selected from the highly hydrophilic amino acid sequences of human HMGB-1.
(4) The first amino acid sequence selected by the present inventors was "Lys Pro Asp Ala Ala Lys Lys Gly Val Val Lys Ala Glu Lys" (SEQ ID NO: 1), spanning from amino acid residues 167 (lysine) to 180 (lysine) of human HMGB-1. This human HMGB-1 amino acid sequence "Lys Pro Asp Ala Ala Lys Lys Gly Val Val Lys Ala Glu Lys" (SEQ ID NO: 1) differs from the corresponding amino acid sequence "Lys Ser Glu Ala Gly Lys Lys Gly Pro Gly Arg Pro Thr Gly" (SEQ ID NO: 2) in human HMGB-2 by nine amino acid residues.

Example 2

Peptide Synthesis

The peptide consisting of the amino acid sequence "Cys Lys Pro Asp Ala Ala Lys Lys Gly Val Val Lys Ala Glu Lys" (SEQ ID NO: 3), which has an extra cysteine at the N-terminus of the amino acid sequence selected in Example 1, was synthesized for the convenience of linking.

First, the peptide having the amino acid sequence "Cys Lys Pro Asp Ala Ala Lys Lys Gly Val Val Lys Ala Glu Lys" (SEQ ID NO: 3) was synthesized by the solid-phase synthesis method with t-butoxycarbonyl amino acids using the Applied Biosystems Model 430A peptide synthesizer according to the instruction manual.

The synthesized peptide was cleaved from the resins by the hydrogen fluoride method in the presence of dimethylsulfide, p-thiocresol, m-cresol, and anisole as scavengers to suppress the side reactions.

Then, the scavengers were extracted with dimethyl ether, and the synthesized peptide was extracted with 2N acetic acid.

The peptide was purified by anion exchange column chromatography using anion exchange resin DOWEX 1-X2, and then tested for the main peak pattern by high performance liquid chromatography (HPLC) using an octadecyl (ODS) column.

After concentration by freeze-drying with an evaporator, the peptide was purified by HPLC fractionation and collection. The devices and conditions used in the HPLC purification were as follows: the reverse phase column used was ODS column YMC-D-ODS-5 (20 mm×300 mm; Yamamura Chemical Laboratories); HPLC was carried out at a flow rate of 7.0 ml/min using 0.1% trifluoroacetic acid (TFA) with 0% to 70% acetonitrile gradient; the pump and gradienter used were TWINCLE and GP-A40 (both from JASCO); and the detection was carried out using a UVIDEC-100V detector (210 nm, 1.28 AUFS; JASCO).

The synthetic peptide purified by fractionation was concentrated by freeze-drying with an evaporator. The purity of the resulting synthetic peptide was determined by HPLC analysis. The devices and conditions used in the HPLC analysis were as follows: the reverse phase column used was ODS column YMC-R-ODS-5 (4.9 mm×300 mm; Yamamura Chemical Laboratories); HPLC was carried out at a flow rate of 1.0 ml/min for 25 minutes using 0.1% trifluoroacetic acid (TFA) with 0% to 70% acetonitrile gradient; the pump and gradienter used were TWINCLE and GP-A40 (both from JASCO); and the detection was carried out using a UVIDEC-100V detector (210 nm, 1.28 AUFS; JASCO). The result showed that the purity of the obtained synthetic peptide was almost 100%.

Example 3

Immunogen Preparation 10 mg of a carrier, namely keyhole limpet hemocyanin (KLH) (Calbiochem) or bovine serum albumin (BSA) (Seikagaku Co.), was dissolved in 10 mM potassium dihydrogen phosphate-dipotassium hydrogen phosphate buffer (pH 7.0), and then 150 μl of N,N-dimethylformamide solution containing 2.5% maleimidebenzoyl N-hydroxysuccinimide ester (MBS) (PIERCE) was added thereto. The mixture was incubated at room temperature for 30 minutes while stirring.

The mixture was loaded at 4° C. onto a gel filtration column (Sephadex G-25 column (Pharmacia LKB)) pre-equilibrated with 10 mM potassium dihydrogen phosphate-dipotassium hydrogen phosphate buffer (pH 7.0). The absorbance was monitored at 280 nm to collect the MBS-carrier conjugate fraction.

The pH of the MBS-carrier conjugate fraction was adjusted to 7.0 using trisodium phosphate. The peptide "Cys Lys Pro Asp Ala Ala Lys Lys Gly Val Val Lys Ala Glu Lys" (SEQ ID NO: 3) synthesized as described in Example 2 was added to the fraction. The combined solution was mixed and incubated for 150 minutes.

After incubation, the solution was dialyzed three times against water. Then, an immunogen consisting of the carrier-conjugated peptide was obtained by freeze-drying.

Example 4

Preparation of Porcine HMGB-1 and HMGB-2

Porcine HMGB-1 (SEQ ID NO: 4) and HMGB-2 (SEQ ID NO: 5) were prepared from pig thymus by the method of Sanders et al. (C. Sanders et al., BBRC (1977) 78: 1034-42).
(1) 500 g of pig thymus was crushed in 600 ml of a buffer containing 140 mM sodium chloride and 0.5 mM PMSF.
(2) Then, the resulting material was centrifuged using a centrifuge, and the supernatant was removed.
(3) A buffer containing 140 mM sodium chloride and 0.5 mM PMSF was added to the precipitate. After stirring, the mixture was centrifuged with a centrifuge, and the resulting supernatant was removed. This washing treatment was repeated twice.
(4) Next, 300 ml of 0.75 M perchloric acid was added to the resulting precipitate. After the mixture was centrifuged with a centrifuge, the resulting supernatant was collected. 400 ml of 0.75 M perchloric acid was added to the remaining precipitate. After this mixture was also centrifuged with a centrifuge, the resulting supernatant was collected. This supernatant was combined with the first supernatant collected. The precipitate was discarded.
(5) 0.75 M perchloric acid was added to the combined supernatant described above, and the total volume was adjusted to 1,000 ml. After centrifugation with a centrifuge, the supernatant was filtered through a glass filter (grade 4).

(6) A mixture of 3,500 ml of acetone and 21 ml of concentrated hydrochloric acid was added to the filtrate obtained by the above-described filtration. Since the mixture became turbid, it was centrifuged with a centrifuge and the resulting supernatant was collected. 2,500 ml of acetone was added to the supernatant. Again, the mixture became turbid. Thus, the mixture was centrifuged with a centrifuge, and the supernatant was removed and the remaining precipitate was collected.

(7) The collected precipitate was air-dried at room temperature.

About 20 mg of the protein fraction containing HMGB-1 and HMGB-2 was obtained by the procedure described above.

(8) The above protein fraction containing HMGB-1 and HMGB-2 was dissolved in 10 ml of 7.5 mM sodium borate buffer (pH 9.0) containing 200 mM sodium chloride, and then thoroughly dialyzed against 7.5 mM sodium borate buffer (pH 9.0) containing 200 mM sodium chloride.

(9) After dialysis, the protein fraction was loaded onto a CM-Sephadex C25 column pre-equilibrated with 7.5 mM sodium borate buffer (pH 9.0). Then, cation exchange chromatography was carried out by eluting the column with 7.5 mM sodium borate buffer (pH 9.0) containing 200 mM sodium chloride.

(10) The mobility determined by subsequent SDS-polyacrylamide gel electrophoresis using 15% gel suggested that the eluted fractions marked with "A" and "B" contained porcine HMGB-1 and the eluted fractions marked with "C" and "D" contained porcine HMGB-2 as shown in FIG. 1.

(11) Thus, the eluted fractions marked with "A" and "B" in FIG. 1 were combined together, while the eluted fractions marked with "C" and "D" were combined together.

Example 5

Preparation of Human HMGB-1 and HMGB-2

Human HMGB-1 (SEQ ID NO: 6) and HMGB-2 (SEQ ID NO: 7) were purified from HL60 cells according to the reference (P. Cabart et al., Cell Biochemistry and Function (1995) 13: 125-133).

(1) HL60 cells were cultured in 300 ml of RPMI1640 (GIBCO) containing 10% inactivated fetal calf serum (FCS: GIBCO) for about one week.

(2) The cultured HL60 cells were harvested and washed with RPMI1640. Then, the cells were cultured in 3 L of PFHM-II (Invitrogen) for about two weeks.

(3) Next, the resulting culture supernatant was loaded onto Heparin-Sepharose (Sigma) pre-equilibrated with PBS.

(4) After thorough washing with PBS, the elution was conducted with PBS containing 0.5 M sodium chloride. The elution was monitored by absorbance at 280 nm, and fractions exhibiting absorbance were pooled. The pool was thoroughly dialyzed against 5 mM borate buffer (pH 9.0) containing 0.2 M sodium chloride.

The dialyzed pool was loaded onto to CM-Sephadex C25 (Pharmacia) pre-equilibrated with 7.5 mM borate buffer (pH 9.0). Then, the elution was conducted with 7.5 mM sodium borate buffer (pH 9.0) containing 200 mM sodium chloride. The result was similar to that shown in Example 4.

Example 6

Preparation of Polyclonal Antibody

A polyclonal antibody was prepared by the procedure described below using as an immunogen porcine HMGB-1 prepared as described in Example 4.

[1] Immunization of Animals (1) The porcine HMGB-1 immunogen prepared as described in Example 4 was dissolved at 100 µg/ml in physiological saline (aqueous solution of 0.9% sodium chloride), and combined with an equal volume of Freund's complete adjuvant. A 0.5-ml aliquot of the resulting emulsion was injected into a chicken (Asahi Techno Glass Co.) at the base of a wing.

(2) Two weeks after the primary immunization, the above-described immunogen was dissolved at 100 µg/ml in physiological saline, and combined with an equal volume of Freund's incomplete adjuvant. A 0.5-ml aliquot of the resulting emulsion was injected as a booster. The booster injection was repeated at two-week intervals.

(3) Six weeks after the primary immunization, the antibody titers in the serum and yolk of immunized chicken were determined every week by enzyme immunoassay (ELISA or EIA). The ELISA procedure is described below.

(3-1) Porcine HMGB-1 was dissolved at 1 µg/ml in physiological saline. 100 µl of the solution was added to each well of a 96-well microplate (Nunc). The plate was left to stand at 37° C. for two hours to immobilize porcine HMGB-1.

(3-2) The microplate was washed with a washing solution (phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 0.05% Tween20). Then, 300 µl of 10 mM potassium dihydrogen phosphate-dipotassium hydrogen phosphate buffer (pH 7.2) containing 1% BSA was added to each well. For blocking, the plate was left to stand at 37° C. for two hours, and then washed with the washing solution again.

(3-3) 100 µl of the yolk of the above-described chicken, which was being tested for antibody production, was dissolved in 900 µl of physiological saline. The solution was then diluted 1,000 times, 10,000 times, and 100,000 times with physiological saline, and 100-µl aliquots were added to wells of the microplate. The plate was left to stand at 37° C. for two hours for the reaction, and then washed with the washing solution again.

(3-4) Furthermore, as a control, 100-µl aliquots of 0.1 M phosphate-buffered physiological saline containing 1% BSA were added to some of the wells of the microplate described above in (3-2). The plate was left to stand at 37° C. for two hours, and then washed with the washing solution.

(3-5) A peroxidase (POD)-labeled anti-chicken IgY antibody (Up-Data) was diluted 5,000 times with phosphate-buffered physiological saline containing 3% BSA, and then 100-µl aliquots were added to the wells of the plate of (3-3) and (3-4). The plate was left to stand at 37° C. for two hours for the reaction.

(3-6) After the plate was washed with the washing solution, 100 µl of a peroxidase reaction solution (which was prepared immediately before use, by combining 2 µl of 1.7% hydrogen peroxide with 1 ml of 50 mM disodium hydrogen phosphate-24 mM citrate buffer containing 3 mM 2,2'-azinobis(3-ethylbenzothiazoline-6-sulfonic acid) (ABTS)) was added to each well. The plate was incubated at room temperature. After 15 minutes, 150 µl of 6N sulfuric acid was added to each well to stop the reaction.

(3-6) The absorbance was measured at 415 nm using an EIA plate reader (Bio-Rad).

(4) The antibody titer reached a plateau 12 weeks after the primary immunization. Then, the antibody (IgY) was obtained from the yolk of the immunized chicken.

(5) 10 ml of the yolk was combined with 40 ml of TBS (0.14 M NaCl, 0.01 M Tris/HCl (pH 7.4), 0.01% NaN$_3$). After stirring well, the mixture was centrifuged, and the resulting supernatant was collected.
(6) Next, 7.5 ml CaCl$_2$ and 3 ml of dextran sulfate (TBS containing 10% (W/V) dextran sulfate) were added to the supernatant. After stirring for about 30 minutes, the mixture was separated into supernatant and precipitate by centrifugation. The supernatant was collected, and the precipitate was extracted again with TBS. After centrifugation, the resulting supernatant was combined with the previous supernatant, and the total volume was adjusted to 100 ml using TBS.
(7) 20 g of anhydrous sodium sulfate was added thereto. After stirring for 30 minutes, the mixture was centrifuged and the resulting supernatant was removed. Then, the precipitate was dissolved in 10 ml of TBS. After adding PBS, the solution was dialyzed against PBS. Thus, a globulin fraction was obtained.
(8) Next, the fraction was loaded onto a column immobilized with porcine HMGB-1 prepared as described in Example 4. The procedure of affinity chromatography is described below.
(8-1) 4 mg of porcine HMGB-1 prepared in Example 4 was reacted with 2 g of CNBr-Sepharose (Pharmacia Biotech) according to the instruction manual. Thus, a column immobilized with the peptide described above was prepared for affinity chromatography.
(8-2) The fraction (polyclonal antibody) concentrated as described in (7) was loaded onto the column pre-equilibrated with phosphate-buffered physiological saline.
(8-3) The column was thoroughly washed with phosphate-buffered physiological saline, and then 0.1 M acetate buffer (pH 3.0) was loaded thereto.
(8-4) The eluted fractions were collected, dialyzed against phosphate-buffered physiological saline, and then concentrated.

The polyclonal antibody that binds to porcine HMGB-1 was fractionated and collected by affinity chromatography as described above.
(9) The chicken anti-porcine HMGB-1 polyclonal antibody prepared by the procedure described above could bind to human HMGB-1 and -2. In this experiment, the antibody was prepared by affinity purification. However, the antibody may be prepared without affinity purification.

Example 7

Antibody that Binds to Human High Mobility Group 1 but not to Human High Mobility Group 2

A polyclonal antibody that binds to human HMGB-1 but not to human HMGB-2 was prepared by the method described below.

Antibody reactive to HMGB-2 was absorbed by loading the polyclonal antibody prepared in Example 6 onto a column immobilized with porcine HMGB-2 prepared in Example 4. The procedure is described below.
(1) 4 mg of porcine HMGB-2 prepared in Example 4 was reacted with 2 g of CNBr-Sepharose (Pharmacia Biotech) according to the instruction manual. Thus, a column immobilized with HMGB-2 described above was prepared as an HMGB-2 absorption column.
(2) The fraction (polyclonal antibody) concentrated as described in Example 6 was loaded onto the column pre-equilibrated with phosphate-buffered physiological saline.
(3) The flow-through fraction was collected, dialyzed against phosphate-buffered physiological saline, and then concentrated.

The polyclonal antibody that bound to porcine HMGB-1 but not to porcine HMGB-2 was fractionated and collected by affinity chromatography as described above.

The chicken anti-porcine HMGB-1 polyclonal antibody prepared by the procedure described above binds to human HMGB-1 but not to human HMGB-2.

Example 8

Reactivity of Anti-HMGB-1 Polyclonal Antibody to the Peptide

The anti-porcine HMGB-1 polyclonal antibody prepared in Example 6 was tested for the reactivity to the peptide antigen prepared in Example 3.
(1) The peptide antigen prepared in Example 3 was dissolved at 1 µg/ml in physiological saline. A 100-µl aliquot of the solution was added to each well of a 96-well microplate (Nunc). The plate was left to stand at 37° C. for two hours to immobilize the peptide antigen.
(2) The microplate was washed with a washing solution (phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 0.05% Tween20). Then, 300 µl of 10 mM potassium dihydrogen phosphate-dipotassium hydrogen phosphate buffer (pH 7.2) containing 1% BSA was added to each well. The plate was left to stand at 37° C. for two hours for blocking, and then washed with the washing solution again.
(3) 100 µl of the yolk of the above-described chicken, which was being tested for antibody production, was dissolved in 900 µl of physiological saline. The solution was then diluted 1,000 times, 10,000 times, and 100,000 times with physiological saline, and 100-µl aliquots were added to wells of the microplate. The plate was left to stand at 37° C. for two hours for the reaction, and then washed with the washing solution again.
(4) Furthermore, as a control, 100-µl aliquots of 0.1 M phosphate-buffered physiological saline containing 1% BSA were added to some of wells of the microplate described above in (2). The plate was left to stand at 37° C. for two hours, and then washed with the washing solution.
(5) A peroxidase (POD)-labeled anti-chicken IgY antibody (Up-Data) was diluted 5,000 times with phosphate-buffered physiological saline containing 3% BSA, and then 100-µl aliquots were added to the wells of the plate of (3) and (4). The plate was left to stand at 37° C. for two hours for the reaction.
(6) After the plate was washed with the washing solution, 100 µl of a peroxidase reaction solution (which was prepared immediately before use by combining 2 µl of 1.7% hydrogen peroxide with 1 ml of 50 mM disodium hydrogen phosphate-24 mM citrate buffer containing 3 mM 2,2'-azinobis(3-ethyl-benzothiazoline-6-sulfonic acid) (ABTS)) was added to each well. The plate was incubated at room temperature. After 15 minutes, 50 µl of 6N sulfuric acid was added to each well to stop the reaction.
(7) The absorbance was measured at 415 nm using an EIA plate reader (Bio-Rad).

Figure 2:
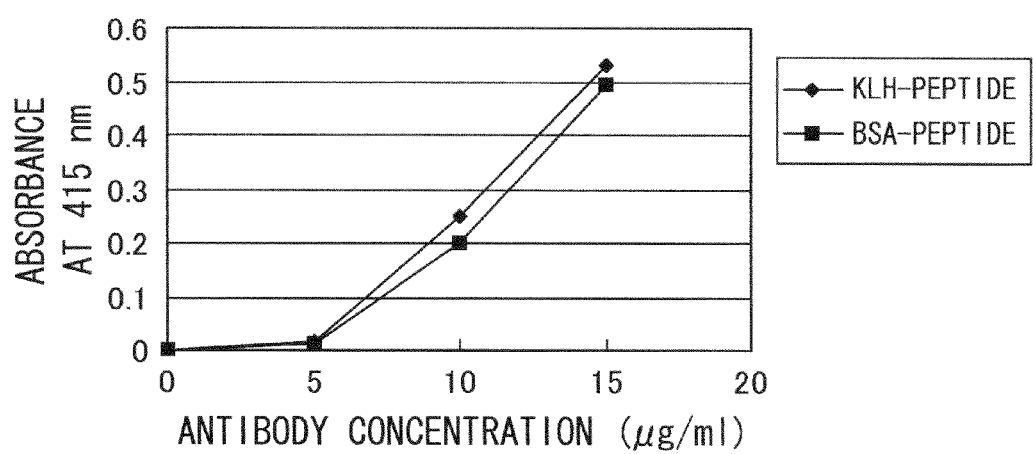
FIG. 2 shows the ELISA result for the reactivity of an anti-porcine HMGB-1 polyclonal antibody to the sequence spanning from amino acid residues 167 (lysine) to 180 (lysine) of human HMGB-1. The immobilized antigen was added with an extra cysteine at its N-terminus and conjugated with keyhole limpet hemocyanin (KLH) or bovine serum albumin (BSA) as a carrier. The horizontal axis indicates the concentration of an anti-porcine HMGB-1 polyclonal antibody added in ELISA. The vertical axis indicates the amount of anti-porcine HMGB-1 polyclonal antibody bound to the antigen, which was detected as an absorbance value using peroxidase (POD)-labeled anti-chicken IgY antibody and peroxidase reaction mixture in ELISA. The anti-porcine HMGB-1 polyclonal antibody reacted in a concentration-dependent manner to the peptide antigen, regardless of the type of carrier conjugated to the antigen. The details of the method are described in Example 8.

The result is shown in FIG. 2. The signal was stronger in higher dilution folds. This clearly shows that the polyclonal antibody prepared using HMGB-1 contained an antibody against the peptide antigen.

Example 9

Preparation of Polyclonal Antibody

A polyclonal antibody was prepared by the procedure described below using the peptide antigen prepared as the immunogen in Example 3.

[1] Immunization of Animals
(1) The immunogen was prepared in Example 3 as described above by conjugating the peptide "Cys Lys Pro Asp Ala Ala Lys Lys Gly Val Val Lys Ala Glu Lys" (SEQ ID NO: 3) with BSA. The resulting conjugate was dissolved at 100 µg/ml in physiological saline (aqueous solution of 0.9% sodium chloride), and combined with an equal volume of Freund's complete adjuvant. A 0.5-ml aliquot of the resulting emulsion was injected into a chicken (Asahi Techno Glass Co.) at the base of a wing.
(2) Two weeks after the primary immunization, the above-described immunogen was dissolved in physiological saline to be 100 µg/ml, and combined with an equal volume of Freund's incomplete adjuvant. A 0.5-ml aliquot of the resulting emulsion was injected as a booster. The booster injection was repeated at two-week intervals.
(3) Six weeks after the primary immunization, the antibody titers in the serum and yolk of the immunized chicken were determined every week by enzyme immunoassay (ELISA or EIA). The ELISA procedure is described below.
(3-1) The peptide prepared in Example 3 was conjugated with KLH. The resulting conjugate was dissolved at 1 µg/ml in physiological saline. 100 µl of the solution was added to each well of a 96-well microplate (Nunc). The plate was left to stand at 37° C. for two hours to immobilize the peptide-KLH.
(3-2) The microplate was washed with a washing solution (phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 0.05% Tween20). Then, 300 µl of 10 mM potassium dihydrogen phosphate-dipotassium hydrogen phosphate buffer (pH 7.2) containing 1% BSA was added to each well. The plate was left to stand at 37° C. for two hours for blocking, and then washed with the washing solution again.
(3-3) 100 µl of the yolk of the above-described chicken, which was being tested for antibody production, was dissolved in 900 µl of physiological saline. The solution was then diluted 1,000 times, 10,000 times, and 100,000 times with physiological saline, and 100-µl aliquots were added to wells of the microplate. The plate was left to stand at 37° C. for two hours for the reaction, and then washed with the washing solution again.
(3-4) Furthermore, as a control, 100-µl aliquots of 0.1 M phosphate-buffered physiological saline containing 1% BSA were added to some of wells of the microplate described above in (3-2). The plate was left to stand at 37° C. for two hours, and then washed with the washing solution.
(3-5) A peroxidase (POD)-labeled anti-chicken IgY antibody (Up-Data) was diluted 5,000 times with phosphate-buffered physiological saline containing 3% BSA, and then 100-µl aliquots were added to the wells of the plate of (3-3) and (3-4). The plate was left to stand at 37° C. for two hours for the reaction.
(3-6) After the plate was washed with the washing solution, 100 µl of a peroxidase reaction solution (which was prepared immediately before use by combining 2 µl of 1.7% hydrogen peroxide with 1 ml of 50 mM disodium hydrogen phosphate-24 mM citrate buffer containing 3 mM 2,2'-azinobis(3-ethyl-benzothiazoline-6-sulfonic acid) (ABTS)) was added to each well. The plate was incubated at room temperature. After 15 minutes, 150 µl of 6N sulfuric acid was added to each well to stop the reaction.
(3-7) The absorbance was measured at 415 nm using an EIA plate reader (Bio-Rad).

(4) The antibody titer reached a plateau 12 weeks after the primary immunization. Then, the antibody (IgY) was obtained from the yolk of the immunized chicken.
(5) 10 ml of the yolk was combined with 40 ml of TBS (0.14 M NaCl, 0.01 M Tris/HCl (pH 7.4), 0.01% NaN$_3$). After stirring well, the mixture was centrifuged, and the resulting supernatant was collected.
(6) Next, 7.5 ml CaCl$_2$ and 3 ml of dextran sulfate (TBS containing 10% (W/V) dextran sulfate) were added to the supernatant. After stirring for about 30 minutes, the mixture was separated into supernatant and precipitate by centrifugation. The supernatant was collected, and the precipitate was extracted again with TBS. After centrifugation, the resulting supernatant was combined with the previous supernatant, and the total volume was adjusted to 100 ml using TBS.
(7) 20 g of anhydrous sodium sulfate was added to the supernatant. After stirring for 30 minutes, the mixture was centrifuged and the resulting supernatant was removed. Then, the precipitate was dissolved in 10 ml of TBS. After adding PBS, the solution was dialyzed against PBS. Thus, a globulin fraction was obtained.
(8) Next, the fraction was loaded onto a column immobilized with the peptide prepared as described in Example 2. The procedure of affinity chromatography is described below.
(8-1) 10 mg of the peptide prepared in Example 2 was reacted with 2 g of CNBr-Sepharose (Pharmacia Biotech) according to the instruction manual. Thus, a column immobilized with the peptide described above was prepared for affinity chromatography.
(8-2) The fraction (polyclonal antibody) concentrated as described in (7) was loaded onto a column pre-equilibrated with phosphate-buffered physiological saline.
(8-3) The column was thoroughly washed with phosphate-buffered physiological saline, and then 0.1 M acetate buffer (pH 3.0) was loaded thereto.
(8-4) The eluted fractions were collected, dialyzed against phosphate-buffered physiological saline, and then concentrated.
The polyclonal antibody that binds to the peptide was fractionated and collected by affinity chromatography as described above.
(9) The chicken polyclonal antibody prepared by the procedure described above can bind to human HMGB-1 but not to human HMGB-2, which exhibits high homology to human HMGB-1.
In this experiment, the antibody was prepared by affinity purification. However, without affinity purification, the antibody can be expected to have a comparable effect when used in an appropriate amount.

Example 10

Assessment of Anti-Peptide Polyclonal Antibody for the Reactivity to Human HMGB-1 and HMGB-2

The anti-peptide polyclonal antibody prepared in Example 9 was assessed by Western blotting to test the reactivity to human HMGB-1 and -2.
1. Western Blotting
Reactivity of the Anti-Peptide Polyclonal Antibody Prepared in Example 9
(1) Human HMGB-1 (1 mg/ml) and HMGB-2 (1 mg/ml) prepared in Example 5 were combined at a ratio of 1:1. Then, the mixture was combined with a sample buffer at a ratio of 1:1.

(2) This sample was electrophoresed using 15% SDS-polyacrylamide gel. The electrophoresis was carried out at a current of 20 mA for 180 minutes using a barbital buffer (pH 8.8) as an electrophoresis buffer.
(3) After the electrophoresis described above in (2), the sample was transferred by the dry method using the NovaBlot Electrophoretic Transfer Kit (Pharmacia LKB) according to the instruction manual. First, the gel after electrophoresis was arranged in the transfer apparatus. Then, a nitrocellulose membrane (9 cm×9 cm; Bio-Rad) was placed on the gel, and the sample was transferred at an electric current of 60 mA for two hours using a transfer buffer consisting of 48 mM Tris (hydroxymethyl)aminomethane, 39 mM glycine, 0.0357% (W/V) sodium dodecyl sulfate (SDS), and 20% (V/V) methanol.
(4) The nitrocellulose membrane after transfer was blocked overnight at 4° C. by soaking in 20 ml of phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 1% BSA.
(5) Next, the membrane was washed in 20 ml of a washing solution (phosphate-buffered physiological saline containing 0.05% Tween20) while shaking for ten minutes. This step was repeated three times.
(6) 80 μg of the polyclonal antibody prepared in Example 9 was dissolved in 20 ml of phosphate-buffered physiological saline containing 1% BSA. The nitrocellulose membrane treated as described above in (5) was soaked in the solution at room temperature for two hours for the reaction.
(7) The nitrocellulose membrane treated as described above in (6) was washed in 20 ml of the washing solution while shaking for ten minutes. This step was repeated three times.
(8) Next, a peroxidase-labeled anti-chicken IgY antibody (Up Data) was diluted 500 times with phosphate-buffered physiological saline containing 3% BSA to prepare a 20-ml solution. The nitrocellulose membrane described above in (7) was soaked in the solution at room temperature for two hours for the reaction.
(9) The nitrocellulose membrane was washed in 20 ml of the washing solution while shaking for ten minutes. This step was repeated three times.
(10) The nitrocellulose membrane described above in (9) was soaked in 20 ml of phosphate-buffered physiological saline containing 0.025% 3,3'-diaminobenzidine tetrahydrochloride and 0.01% hydrogen peroxide at room temperature for 15 minutes for color development.

The polyclonal antibody prepared in Example 9 was assessed by Western blotting using the procedure described above.
2. Experimental Results
(1) Results of Western Blotting
The result of Western blotting using the polyclonal antibody described above is shown in FIG. 3. In this figure, "1" shows the result of the polyclonal antibody (the polyclonal antibody prepared in Example 9). "2" shows the result obtained by reacting the peroxidase-labeled anti-chicken IgY antibody (Up-Data) alone. "3" shows the positions of human HMGB-1 and -2 determined by reacting the anti-porcine HMGB-1 polyclonal antibody prepared in Example 6.

Figure 3:
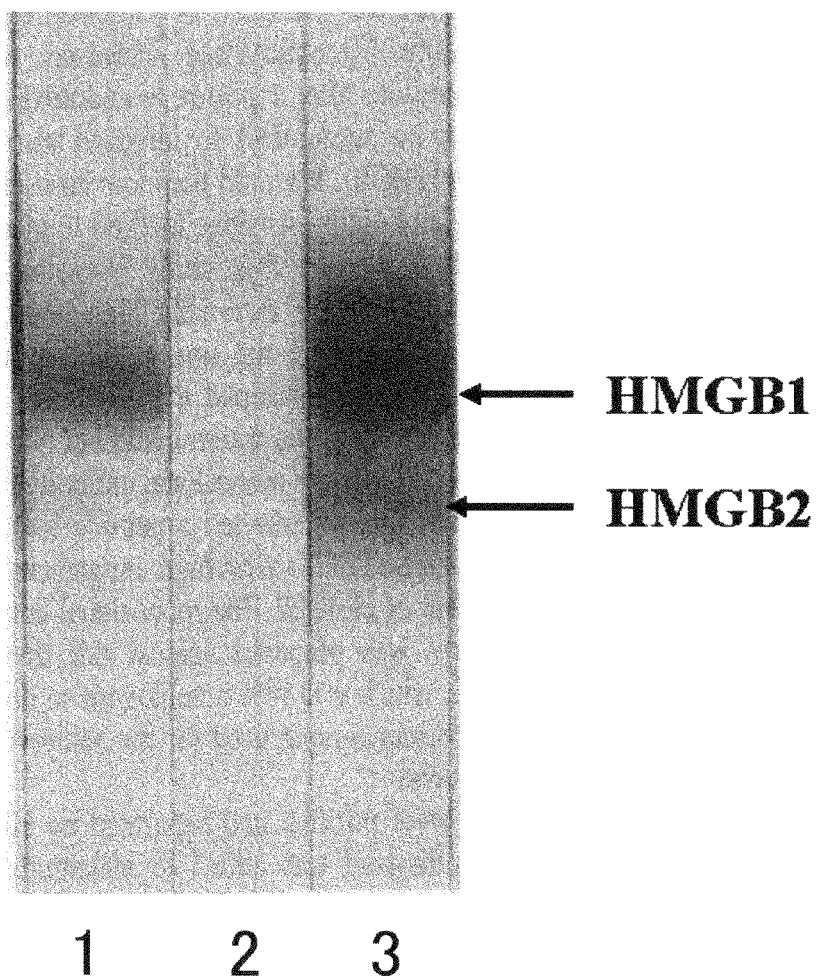
FIG. 3 shows the result of assessing the reactivity of a polyclonal antibody to human HMGB-1 and HMGB-2 by Western blotting. The polyclonal antibody was obtained using the antigen consisting of the sequence spanning from amino acid residues 167 (lysine) to 180 (lysine) of human HMGB-1, which also had an extra cysteine at its N-terminus and was conjugated with keyhole limpet hemocyanin (KLH) or bovine serum albumin (BSA) as a carrier. "1" shows the result obtained using the polyclonal antibody (the polyclonal antibody prepared in Example 9). "2" shows the result obtained by reacting the peroxidase-labeled anti-chicken IgY (Up Data) alone. "3" shows determination of the positions of human HMGB-1 and -2 using the anti-porcine HMGB-1 polyclonal antibody prepared in Example 6.

According to FIG. 3, color development was undetectable at the positions of the human HMGB-1 and HMGB-2 bands in the control shown in "2", in which the peroxidase-labeled anti-chicken IgY antibody alone was reacted without the polyclonal antibody. This shows that nonspecific color development did not occur in each of the Western blots described above.

As seen in "1", the polyclonal antibody prepared in Example 9 caused color development at the band position of human HMGB-1 but not at the band position of human HMGB-2. This demonstrates that the anti-peptide polyclonal antibody prepared in Example 9 was reactive to human HMGB-1 but not to human HMGB-2.

Example 11

Preparation of Monoclonal Antibody

Monoclonal antibodies that can be used in the present invention are available by the procedure described below. Using human HMGB-1 prepared in Example 5 as an immunogen, monoclonal antibodies were prepared by the following procedure.
1. Immunization of Animals
The human HMGB-1 immunogen prepared as described above in Example 5 was dissolved at 100 μg/ml in physiological saline (aqueous solution of 0.9% sodium chloride), and combined with an equal volume of Freund's complete adjuvant. 0.5 ml of the resulting emulsion was injected into eight-week-old female BALB/c mice (Charles River Japan) subcutaneously in the abdomen. Two weeks after the primary immunization, the above-described immunogen was dissolved at 100 μg/ml in physiological saline, and combined with an equal volume of Freund's incomplete adjuvant. A 0.5-ml aliquot of the resulting emulsion was injected as a booster. The booster injection was repeated at two-week intervals. Six weeks after the primary immunization, the antibody titers in the immunized mice were determined every week by enzyme immunoassay (ELISA or EIA). Details of the ELISA procedure are described below in (1). The antibody titers reached a plateau 18 weeks after the primary immunization. Then, 0.5 ml of human HMGB-1 dissolved at 800 μg/ml in physiological saline as described in Example 5 was injected into the immunized mice subcutaneously in the abdomen. Spleens were isolated from the mice after three days.
(1) ELISA
Human HMGB-1 was dissolved at 1 μg/ml in physiological saline. A 100-μl aliquot of the solution was added to each well of a 96-well microplate (Nunc). The plate was left to stand at 37° C. for two hours to immobilize human HMGB-1. The microplate was washed with a washing solution (phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 0.05% Tween20). Then, 300 μl of 10 mM potassium dihydrogen phosphate-dipotassium hydrogen phosphate buffer (pH 7.2) containing 1% BSA was added to each well. The plate was left to stand at 37° C. for two hours for blocking, and then washed with the washing solution again. 100 μl of the sera of the above-described mice, which were being tested for antibody production, were dissolved in 900 μl of physiological saline. The serum samples were then diluted 1,000 times, 10,000 times, and 100,000 times with physiological saline, and 100-μl aliquots were added to wells of the microplate. The plate was left to stand at 37° C. for two hours for the reaction, and then washed with the washing solution. Furthermore, as a control, instead of mouse serum, 100-μl aliquots of 0.1 M phosphate-buffered physiological saline containing 1% BSA were added to some of wells of the microplate. The plate was left to stand at 37° C. for two hours, and then washed with the washing solution: A peroxidase (POD)-labeled anti-mouse IgG antibody (Amersham) was diluted 5,000 times with phosphate-buffered physiological saline containing 3% BSA, and then 100-μl aliquots were added to the wells of each microplate. The plate was left to stand at 37° C. for two hours for the reaction, and then washed with the washing solution. 100 μl of a peroxidase reaction solution (which was prepared immediately before use by combining 2 μl of 1.7% hydrogen peroxide with 1 ml of 50 mM disodium hydrogen phosphate-24 mM citrate buffer containing 3 mM 2,2'-azinobis(3-ethyl-benzothiazoline-6-sulfonic acid) (ABTS)) was added to each well. The plate was incubated at room temperature. After 15 minutes, 150 μl of 6N sulfuric acid was added to each well to stop the reaction. The absorbance was measured at 415 nm using an EIA plate reader (Bio-Rad).

2. Expansion of Myeloma

Cells of the P3-X63-Ag8-U1 line (Japanese Collection of Research Bioresources Cell Bank 9085), which is a hypoxanthine-guanine-phosphoribosyl transferase-deficient myeloma line derived from BALB/c mouse, were expanded in RPMI1640 tissue culture medium (BioCell) supplemented with glutamine, penicillin, and streptomycin containing 10% fetal bovine serum. More specifically, the myeloma cells were expanded in a medium-sized cell culture bottle (Nunc; 200 ml) until about 80% confluent on the bottom surface of the bottle. The cell count was determined by the trypan blue exclusion method and with a hemocytometer.

3. Cell Fusion

The spleens isolated from the immunized mice, which are described above in 1, were thoroughly ground on a stainless steel mesh #200, and washed by filtration using serum-free RPMI1640. Then, the spleen cells were separated by centrifugation at 200×g, and combined with serum-free cells of the myeloma line P3-X63-Ag8-U1 at a ratio of 5:1. The mixture was centrifuged. The mixed cells were slowly suspended in RPMI1640 containing 50% polyethylene glycol 1500 (PEG1500; Roche Diagonostics). The suspension was gradually diluted with RPMI1640 until the final polyethylene glycol concentration became 5%. The cells were separated by centrifugation and then gradually dispersed in an expansion medium, which was an S-Clone medium (Sanko Junyaku Co.) containing 5% hybridoma cloning factor (Origen). Then, $10^6$ cells (100 μl) were plated into each well of a flat-bottomed 96-well microplate (Nunc), and cultured at 37° C. under 5% carbon dioxide. One day after the cell fusion, 100 μl of a HAT medium (the above-described expansion medium supplemented with 0.01 mM hypoxanthine, 1.6 μM thymidine, and 0.04 μM aminopterin; all from Tokyo Kasei) was added to each well. For the following three days, about half of the HAT medium was changed with fresh medium every day. Then, the medium change was carried out in the same way every two to three days.

The cells were observed under a microscope. The result showed that hybridoma (fused cell) clones appeared after ten days. The culture media in the wells were screened by ELISA 14 days after cell fusion to test the production of antibodies that recognize human HMGB-1. The ELISA procedure was the same as described above in 1 (1). Hybridomas that produce human HMGB-1-recognizing antibodies as determined by the screening were expanded in 24-well plates. When the cell density increased, the culture scale was increased with small-sized bottles and then with medium-sized bottles. The hybridomas were cultured and maintained in HT medium (HAT medium without aminopterin and hybridoma cloning factor). Forty hybridomas were identified as desired ones, after the production of antibodies that recognize human HMGB-1 was assessed by ELISA using the same method as described in 1 (1).

4. Hybridoma Subcloning

Each of the above-described hybridomas producing antibody against human HMGB-1 was subcloned by the limiting dilution method. The hybridoma count was determined by the trypan blue exclusion method and with a hemocytometer. Next, the hybridomas were suspended at two different cell densities, 0.5 and 1 viable cell/100 μl, in HT medium, and aliquoted (100 μl) into wells of a flat-bottomed 96-well microplate. The hybridomas were grown with a medium change every two to three days. The colonies in each well were counted under a microscope after two weeks, and the hybridomas producing antibody against porcine HMGB-1 were assessed by ELISA with the same procedure described above. Two hybridomas (wells) were found to exist as one colony in a well and to produce such antibody, and thus identified as desired ones.

The prepared hybridomas were transferred into 24-well plates and cultured for two weeks until cell growth became stable. Then, the antibodies produced by the hybridomas were assessed by ELISA for the reactivity to human HMGB-1 prepared in Example 5. The ELISA procedure was the same as described above in 1 (1), except that the protein immobilized onto the 96-well microplate was human HMGB-1 prepared in Example 5 and the sample was the culture supernatant of each hybridoma (each well).

The result showed that twenty of the above-described hybridomas were cell lines producing an antibody that binds to human HMGB-1 described above.

Next, the antibodies produced by the hybridomas were assessed by ELISA for the reactivity to human HMGB-1 or human HMGB-2 prepared in Example 5. The ELISA procedure was the same as described above in 1 (1), except that the protein immobilized onto the 96-well microplate was human HMGB-1 or human HMGB-2 prepared in Example 5, and the samples were the hybridomas (the culture supernatants in the wells).

The assessment result showed that the antibody-producing hybridomas include clones producing antibodies that bind to human HMGB-1 but not to human HMGB-2. The hybridomas were named R08G12G2 and R06G7E10.

5. Production of Monoclonal Antibody

Cells of each of the monoclonal antibody-producing cell lines (hybridomas), which were obtained as described above in 4, were added to a medium-sized bottle (Nunc) and cultured in HT medium until about 80% confluent on the bottom surface of the bottle. Then, the hybridomas were harvested, and collected by centrifugation at 200×g for five minutes. After washing three times with serum-free RPMI1640, the cells were suspended in 2 ml of RPMI1640. 1 ml of the hybridoma suspensions were injected into the peritoneal cavities of male BALB/c mice (Charles River Japan) pretreated with 2,6,10,14-tetramethylpentadecane. This treatment was repeated only when the abdomen was not swollen within two weeks after injection. Ascites was collected from mice exhibiting abdominal swelling. The ascites samples were centrifuged at 200×g for five minutes, and the resulting supernatants containing monoclonal antibody produced by the hybridomas were separated from the hybridomas.

6. Purification of Monoclonal Antibody (1) When the Monoclonal Antibody is IgG 1.8 g of sodium sulfate was added at 22° C. while stirring to 10 ml of each of the monoclonal antibody-containing supernatants produced by the hybridomas and prepared as described above in 5. After sodium sulfate was completely dissolved, the solution was further stirred for one hour for salting out. The solution was centrifuged at 22° C. (7,000×g for 15 minutes). The precipitate separated from the supernatant was dissolved in 2 ml of 40 mM sodium phosphate buffer (pH 8.0) containing 30 mM sodium chloride, and then dialyzed thoroughly against 40 mM sodium phosphate buffer (pH 8.0) containing 30 mM sodium chloride. The resulting insoluble material was removed by centrifugation at 1,000×g for 20 minutes. The solution was loaded at a flow rate of 0.4 ml/min onto a DEAE-cellulose ion exchange column (Serva; 1×10 cm) pre-equilibrated with 40 mM sodium phosphate buffer (pH 8.0) containing 30 mM sodium chloride. The eluate was collected in 2-ml fractions. While checking that the flow-through fraction of the eluate contained immunoglobulin G (IgG) based on the absorbance at 280 nm, the fractions were collected and pooled, and the pooled solution was then concentrated to 2 ml. The concentrate was applied to affinity chromatography using protein A-Sepharose CL-4B (Pharmacia LKB) in order to purify antibody. Thus, the purified monoclonal antibodies were obtained.

(2) When the Monoclonal Antibody is IgM 10 ml of each of the monoclonal antibody-containing supernatants produced by the hybridomas and prepared as described above in 5 was thoroughly dialyzed against 20 mM phosphate buffer (pH 7.5) containing 0.8 M ammonium sulfate. The supernatants after dialysis were loaded onto 1 ml of HiTrap IgM Purification HP (Amersham Biosciences) pre-equilibrated with 20 mM phosphate buffer (pH 7.5) containing 0.8 M ammonium sulfate. After washing thoroughly with 20 mM phosphate buffer (pH 7.5) containing 0.8 M ammonium sulfate, the antibody was eluted with 20 mM phosphate buffer (pH 7.5). Thus, purified monoclonal IgM antibodies were obtained.

Example 12

Assessment of Monoclonal Antibodies for the Reactivity to Human HMGB-1 and -2

The monoclonal antibodies were assessed by Western blotting for the reactivity to human HMGB-1 and -2 prepared in Example 5. As an example, clone R06G7E10 is described below. Other clones were assessed in the same way.

(1) Reactivity of the Monoclonal Antibodies Prepared in Example 11 (Western Blotting)

Human HMGB-1 (1 mg/ml) and HMGB-2 (1 mg/ml) prepared in Example 5 were combined at a ratio of 1:1, and the mixture was combined with a sample buffer at a ratio of 1:1. The sample was electrophoresed using a 15% SDS-polyacrylamide gel. The electrophoresis was carried out at a current of 20 mA for 180 minutes using a barbital buffer (pH 8.8) as the electrophoresis buffer. After the electrophoresis, the sample was transferred by the dry method using NovaBlot Electrophoretic Transfer Kit (Pharmacia LKB) according to the instruction manual. Specifically, the gel after electrophoresis was first arranged in the transfer apparatus. Then, a nitrocellulose membrane (9 cm×9 cm; Bio-Rad) was placed on the gel, and the sample was transferred at an electric current of 60 mA for two hours using a transfer buffer consisting of 48 mM Tris(hydroxymethyl)aminomethane, 39 mM glycine, 0.0357% (W/V) sodium dodecyl sulfate (SDS), and 20% (V/V) methanol.

The nitrocellulose membrane after transfer was blocked overnight at 4° C. by soaking in 20 ml of phosphate-buffered physiological saline (aqueous solution (pH 7.2) containing 5.59 mM disodium hydrogen phosphate, 1.47 mM potassium dihydrogen phosphate, 137 mM sodium chloride, and 2.68 mM potassium chloride) containing 1% BSA. Next, the membrane was washed for ten minutes in 20 ml of a washing solution (phosphate-buffered physiological saline containing 0.05% Tween20) while shaking. This step was repeated three times. 80 µg of the monoclonal antibody prepared in Example 11 was dissolved in 20 ml of phosphate-buffered physiological saline containing 1% BSA. For reaction, the nitrocellulose membrane washed as described above was soaked in the solution at room temperature for two hours. Then, the membrane was washed by shaking in 20 ml of the washing solution for ten minutes. This step was repeated three times.

Next, a peroxidase-labeled anti-mouse IgG antibody (Dako) was diluted 500 times with phosphate-buffered physiological saline containing 3% BSA to prepare a 20-ml solution. For reaction, the nitrocellulose membrane described above was soaked in the solution at room temperature for two hours. The nitrocellulose membrane was washed in 20 ml of the washing solution while shaking for ten minutes. This step was repeated three times. The nitrocellulose membrane described above was soaked in 20 ml of phosphate-buffered physiological saline containing 0.025% 3,3'-diaminobenzidine tetrahydrochloride and 0.01% hydrogen peroxide at room temperature for 15 minutes for color development.

The monoclonal antibody prepared in Example 11 was assessed by Western blotting using the procedure described above.

The result of Western blotting using R06G7E10 described above in 1 is shown in FIG. 4. In this figure, "1" shows the result obtained by reacting the peroxidase-labeled anti-mouse IgG antibody (Dako) alone. "2" shows the result obtained by reacting R06G7E10 (the monoclonal antibody prepared in Example 11). "3" shows the result obtained by reacting the anti-porcine HMGB-1 polyclonal antibody prepared in Example 6.

Figure 4:
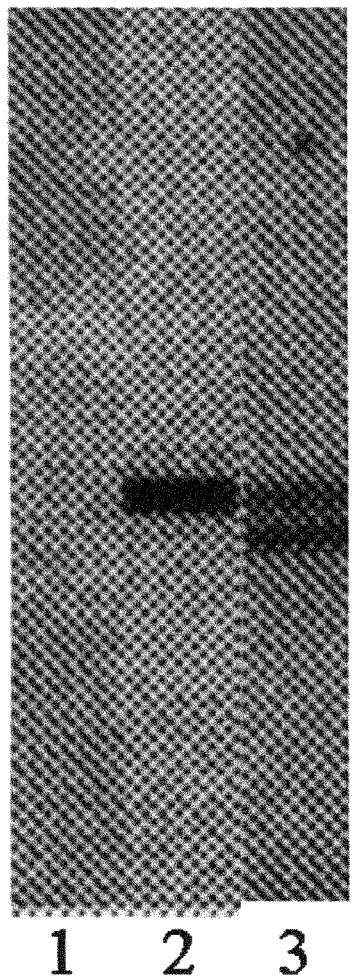
FIG. 4 shows the result of assessing the reactivity of a monoclonal antibody to human HMGB-1 and HMGB-2 by Western blotting. The monoclonal antibody was produced by clone R06G7E10. "1" shows the result obtained by reacting the peroxidase-labeled anti-mouse IgG antibody (Dako) alone. "2" shows the result obtained using R06G7E10 (the monoclonal antibody prepared in Example 11). "3" shows determination of the positions of human HMGB-1 and -2 using the anti-porcine HMGB-1 polyclonal antibody prepared in Example 6.

There was no color development at the band positions of human HMGB-1 and HMGB-2 in the control where the peroxidase-labeled anti-mouse IgG antibody alone was reacted without the monoclonal antibody described in "1" of FIG. 4. This shows that nonspecific color development did not occur in the Western blots described above. As seen in "2", the monoclonal antibody prepared in Example 11 caused color development at the band position of human HMGB-1 but not at the band position of human HMGB-2.

Example 13

Therapeutic Effect of Neutralizing Antibodies on Amyloidosis

When $AgNO_3$ alone was administered to amyloidosis model mice, inflammation was induced, and then amyloid deposition was detected only 14 to 21 days after administration. By contrast, when $AgNO_3$ was administered (or inflammation induced by a certain method) in combination with homogenate liquid derived from the spleens of secondary amyloidosis mice as an amyloid enhancing factor (AEF), amyloid deposition was detected about two to three days after administration. The onset of amyloidosis was observed to be accelerated due to AEF, and such effect persisted for 120 or more days after administration. The present inventors confirmed that HMGB-1 was abundant in the homogenate liquid derived from the spleens of secondary amyloidosis mice, which was used as AEF. Thus, the present inventors tested the effect of anti-HMGB-1 antibody on this phenomenon.

Figure 5:
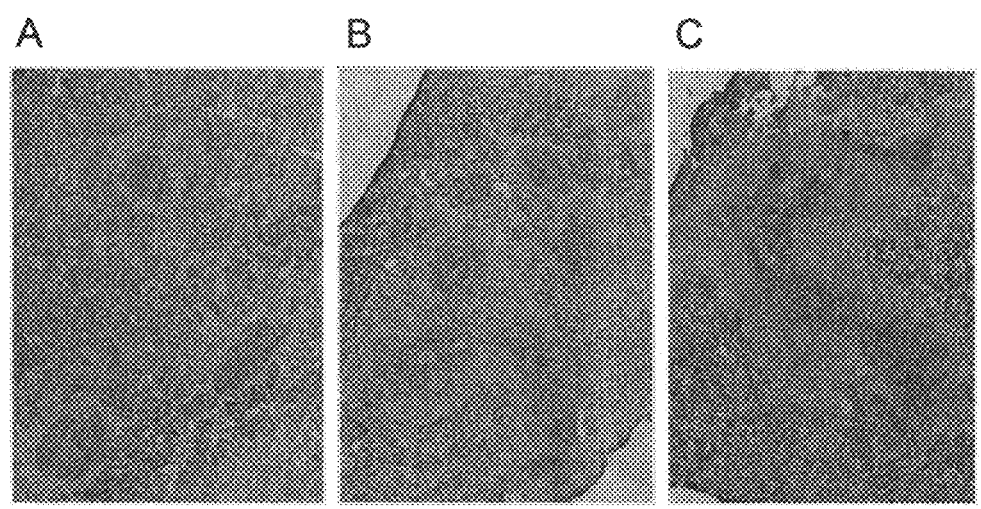
FIG. 5 shows the degree of amyloid deposition in the spleens of amyloidosis model mice. The model was generated by injecting six-week-old male mice of the C3H/HeNCrj strain subcutaneously with 400 µl of 2% $AgNO_3$, and at the same time intraperitoneally with 400 µl of homogenate liquid derived from the spleens of secondary amyloidosis mice (amyloid enhancing factor (AEF)). Amyloid deposition was detected (amyloid was stained red with Congo red) four (B) and seven (C) days after $AgNO_3$ injection and intraperitoneal administration of 400 µl of AEF. In the case of subcutaneous injection of 400 µl of 2% $AgNO_3$ alone (A), the intensity of Congo red stain was found to be weak even seven days after administration.
Figure 6:
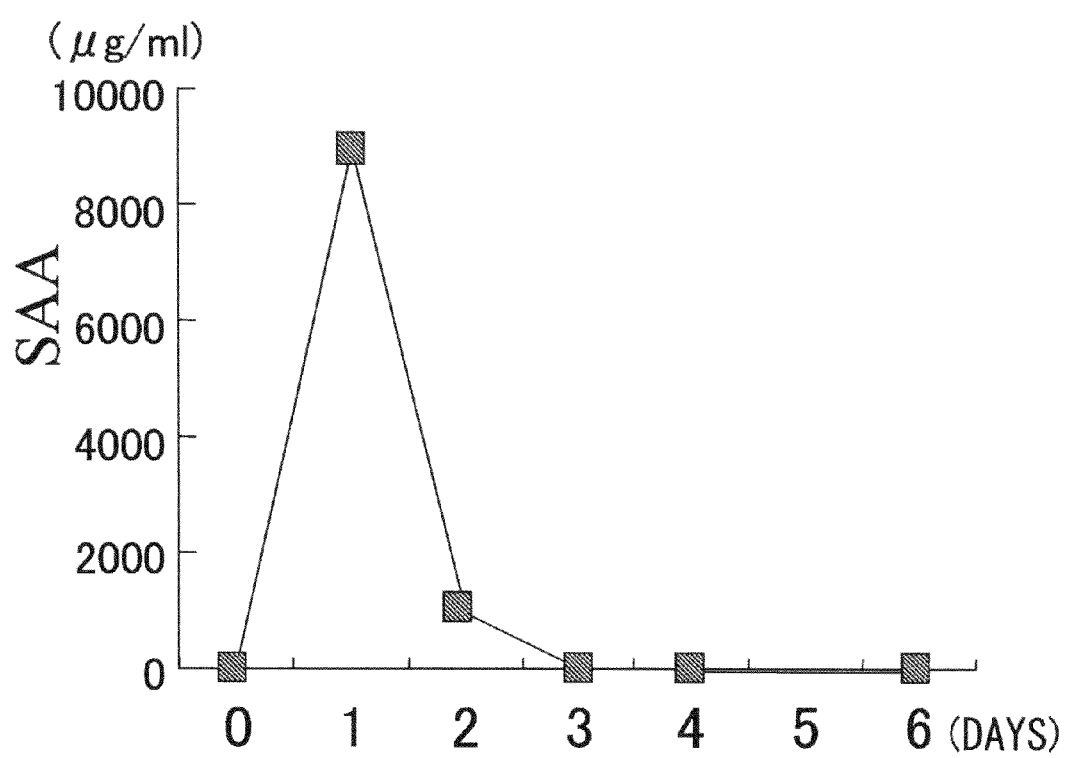
FIG. 6 shows the time course of serum amyloid (SAA) in amyloidosis model mice. The model was generated by injecting six-week-old male mice of the C3H/HeNCrj strain subcutaneously with 400 µl of 2% $AgNO_3$, and at the same time intraperitoneally with 400 µl of homogenate liquid derived from the spleens of secondary amyloidosis mice (amyloid enhancing factor (AEF)). Elevation peak of SAA was observed the day after subcutaneous injection of 400 µl of 2% $AgNO_3$ and intraperitoneal administration of 400 µl AEF.

FIG. 5 shows amyloid deposition in six-week-old male mice of the C3H/HeNCrj strain subcutaneously injected with 400 µl of 2% $AgNO_3$ and intraperitoneally administered with 400 µl of AEF. The time course of serum amyloid protein (SAA) is shown in FIG. 6.

Figure 7:
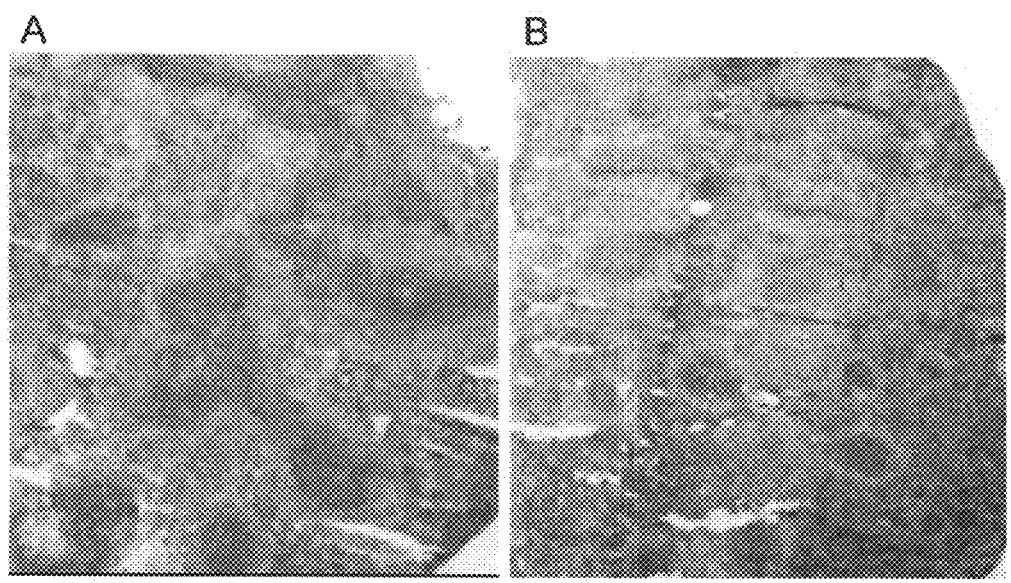
FIG. 7 shows the effect of an anti-HMGB-1 antibody in suppressing amyloid deposition in the spleens of amyloidosis model mice. Six-week-old male mice of the C3H/HeNCrj strain were subcutaneously injected with 400 µl of 2% $AgNO_3$, and intraperitoneally administered with 400 µl of non-treated AEF (A) or homogenate liquid derived from the spleens of secondary amyloidosis mice (B) (amyloid enhancing factor (AEF)) pre-treated with an anti-HMGB-1 antibody (the anti-porcine HMGB-1 polyclonal antibody prepared as described in Example 6). The resulting amyloid deposition in the spleens was compared six days after administration. Amyloid deposition in the spleens was found to be suppressed in the mice administered with anti-HMGB-1 antibody-pre-treated AEF (amyloid was stained red with Congo red).

FIG. 7 shows the result of comparison and assessment of amyloid deposition in mice six days after administration of non-treated AEF or $AgNO_3$ in combination with AEF (homogenate liquid derived from the spleens of secondary amyloidosis mice) pre-treated with an anti-HMGB-1 antibody (the anti-porcine HMGB-1 polyclonal antibody prepared as described in Example 6). As clearly shown, amyloid deposition was suppressed in mice administered with the anti-HMGB-1 antibody-pretreated AEF.

INDUSTRIAL APPLICABILITY

The present invention provides novel agents for treating amyloidosis. The therapeutic agents of the present invention comprise an anti-HMGB-1 antibody that binds to HMGB-1 as an active ingredient.

The invention claimed is:

1. A method for treating secondary systemic amyloidosis, which comprises administering an anti-high mobility group box protein 1 (HMGB-1) antibody to treat secondary systemic amyloidosis in a subject.

2. The method of claim 1, wherein the anti-HMGB-1 antibody binds more strongly to HMBG-1 than to high mobility group box protein 2 (HMGB-2).

3. The method of claim 1, wherein the anti-HMGB-1 antibody does not bind to HMGB-2.

4. The method of claim 1, wherein the anti-HMBG-1 antibody binds a partial peptide comprising the amino acid sequence of SEQ ID NO: 1.

* * * * *

UNITED STATES PATENT AND TRADEMARK OFFICE
CERTIFICATE OF CORRECTION

| | |
|---|---|
| PATENT NO. | : 8,470,325 B2 |
| APPLICATION NO. | : 12/449543 |
| DATED | : June 25, 2013 |
| INVENTOR(S) | : Ando et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this
Twenty-seventh Day of January, 2015

Michelle K. Lee
*Deputy Director of the United States Patent and Trademark Office*